US012714452B2

(12) United States Patent
Finn et al.

(10) Patent No.: US 12,714,452 B2
(45) Date of Patent: Aug. 25, 2026

(54) SURGICAL TUNNELING DEVICES AND METHODS

(71) Applicant: INSPIRE MEDICAL SYSTEMS, INC., Golden Valley, MN (US)

(72) Inventors: Ryan E. Finn, Roseville, MN (US); Lydia R. Anderson, St. Louis Park, MN (US); Kevin Verzal, Lino Lakes, MN (US); Bryan J. Skulsky, Plymouth, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 123 days.

(21) Appl. No.: 18/522,532

(22) Filed: Nov. 29, 2023

(65) Prior Publication Data

US 2024/0216003 A1 Jul. 4, 2024

Related U.S. Application Data

(60) Provisional application No. 63/477,441, filed on Dec. 28, 2022.

(51) Int. Cl.
*A61B 17/32* (2006.01)

(52) U.S. Cl.
CPC .. *A61B 17/32* (2013.01); *A61B 2017/320056* (2013.01)

(58) Field of Classification Search
CPC ........ A61B 17/32; A61B 2017/320056; A61B 17/3468; A61M 25/0194–2025/0197
See application file for complete search history.

(56) References Cited

U.S. PATENT DOCUMENTS 6,582,441 B1 * 6/2003 He ........................ A61N 1/0551 604/59
8,260,394 B2 9/2012 Anderson et al.
8,328,790 B2 12/2012 Chesnin
8,926,646 B2 1/2015 Pandey et al.
9,248,257 B2 2/2016 Martin et al.
10,299,805 B2 5/2019 Germain et al.
11,241,253 B2 2/2022 Vanderpool et al.
2003/0045892 A1 * 3/2003 Kaladelfos ......... A61B 17/0469 606/148
2004/0044348 A1 * 3/2004 Skakoon ............ A61B 17/3415 606/108
2014/0188148 A1 * 7/2014 le Blanc ............. A61M 60/148 606/181
2015/0005570 A1 * 1/2015 Fritz .................. A61B 17/0401 600/16
2016/0235427 A1 * 8/2016 Rudser ............... A61B 17/8875
2017/0259039 A1 * 9/2017 Gordon ............. A61M 25/0668

OTHER PUBLICATIONS

VNS Therapy, LivaNova® Tunneler Model 402 Manual, Published on Jun. 2017, https://www.livanova.com, (Year: 2017), 4 pages.
Codman Specialty Surgical, SiphonGuard® CSF Flow Control Device, https://Integralife.com, (Year: 2018), 16 pages.

(Continued)

*Primary Examiner* — Brigid K Byrd
(74) *Attorney, Agent, or Firm* — Dicke, Billig & Czaja, PLLC

(57) ABSTRACT

Surgical devices and/or methods for forming a pathway in the body of a patient.

21 Claims, 22 Drawing Sheets

(56) References Cited

OTHER PUBLICATIONS

Medtronic Inc., Disposable Subcutaneous Catheter Passers, (Year: 2018), 2 pages.
Codman, Integra LifeSciences Production Corporation, Disposable Catheter Passer, (Year: 2019), 44 pages.
Inspire Sleep Apnea Innovation, System Implant Manual, Inspire IV Implantable Pulse Generator Model 3028, Stimulation Lead Model 4063, Respiratory Sensing Lead Model 4340, https://www.inspiresleep.com, (Year: 2020), 4 pages.
Natus, Neurocritical Care & Neurosurgery Product and Accessory Catalog, Healthcare Solutions With One Thing in Mind. You., https://www.natus.com, (Year: 2021), 64 pages.

* cited by examiner 108
110
104
122

122
106
100
102

104
112
120
116
118
102
114

204
208
242
208
230

246
204
240
222
244
232
245
200
202
200
202

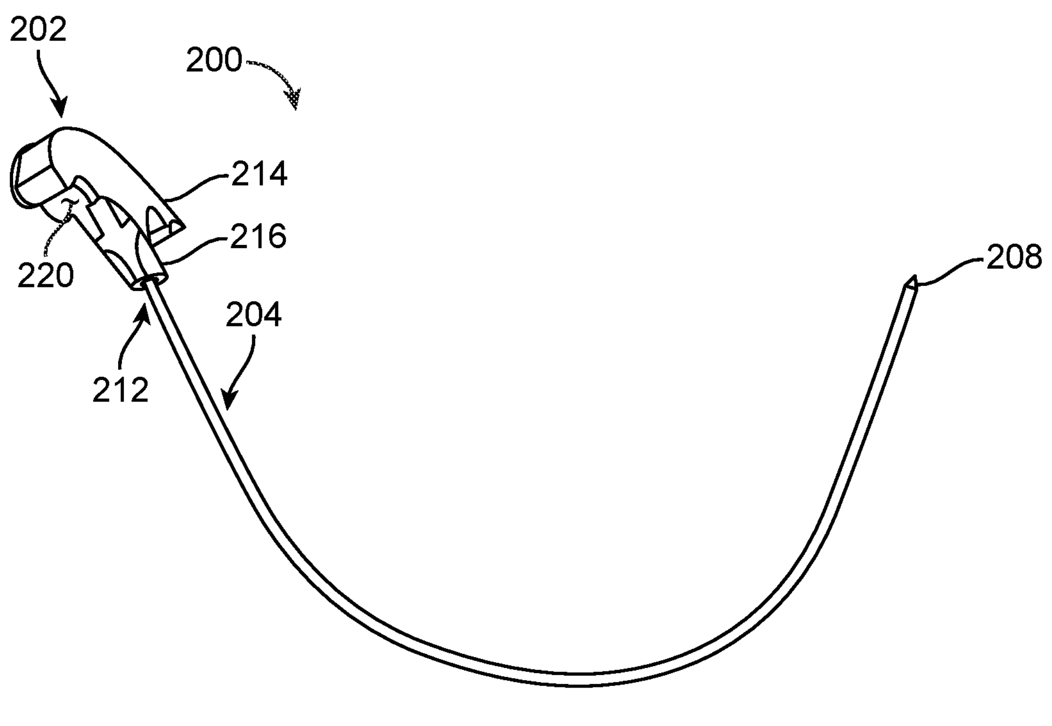
FIG. 2C
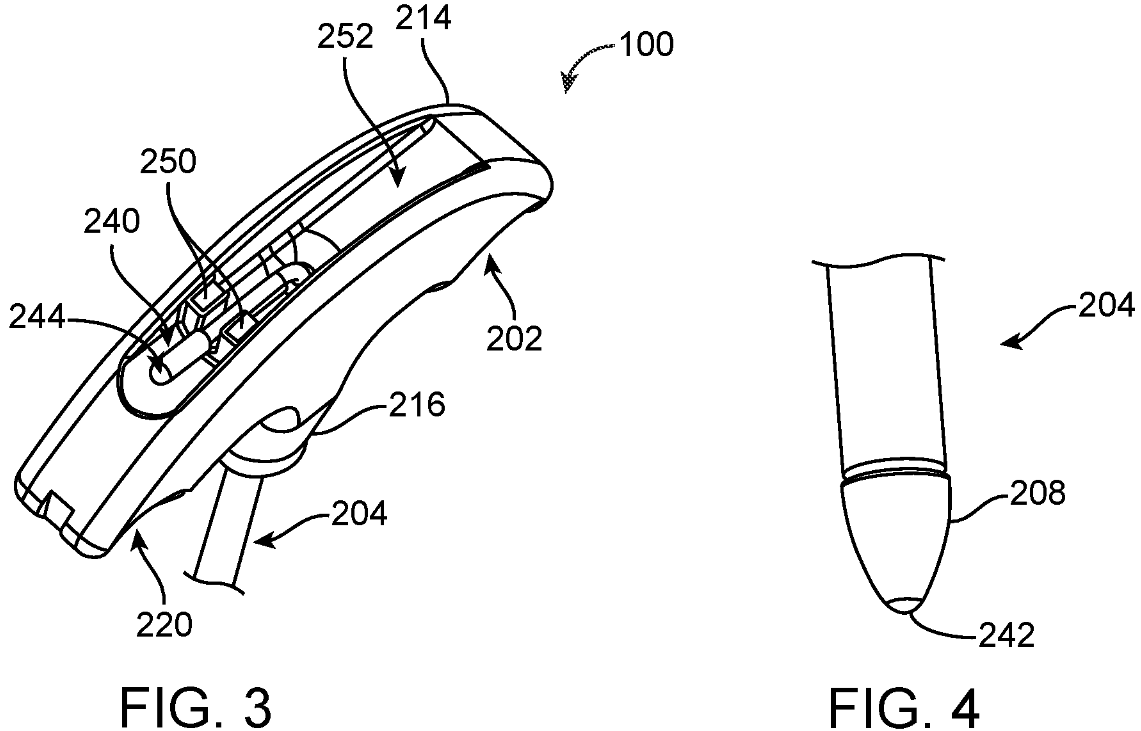
FIG. 3
FIG. 4

FIG. 9A
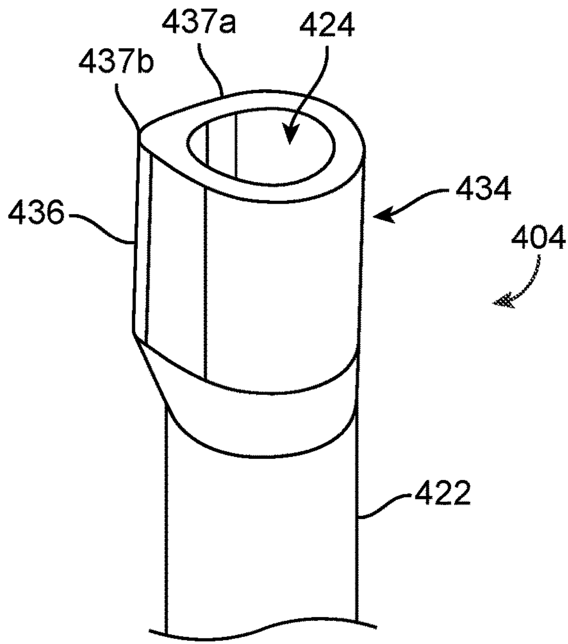
FIG. 9B
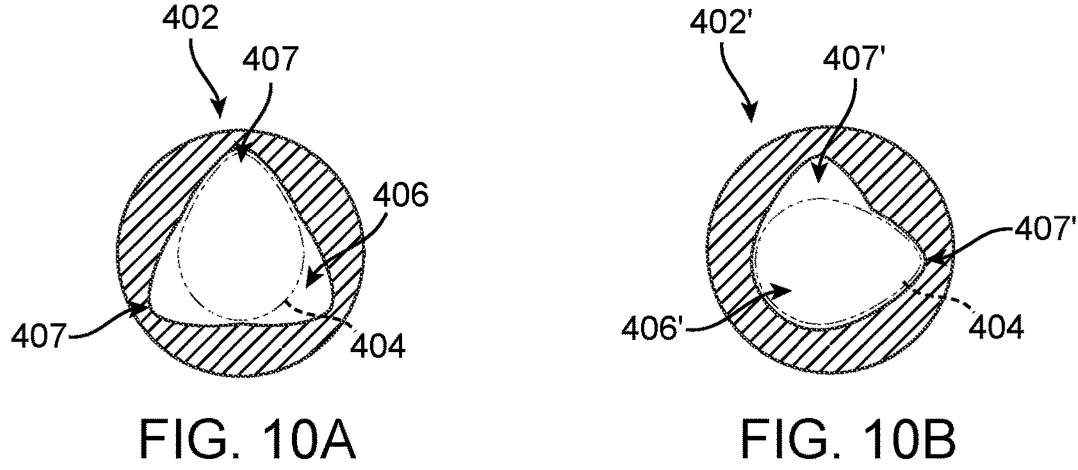
FIG. 10A
FIG. 10B

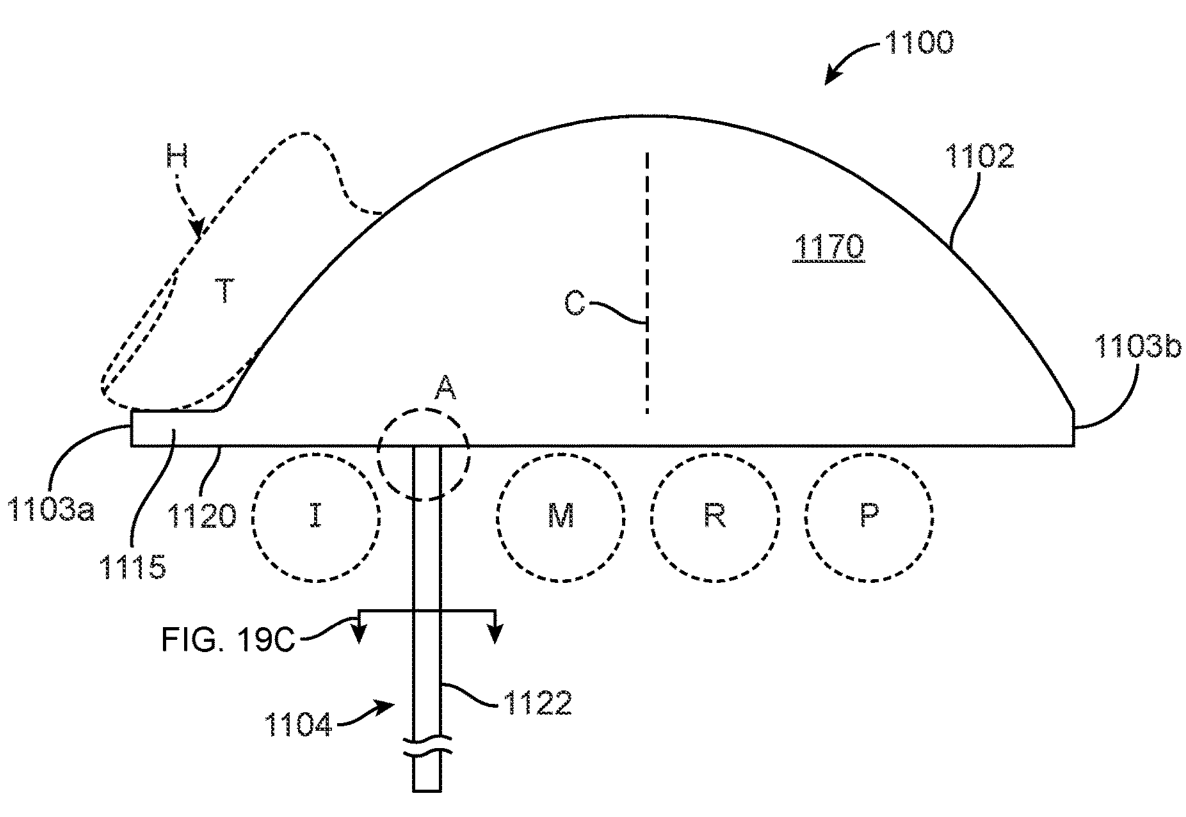
FIG. 19A
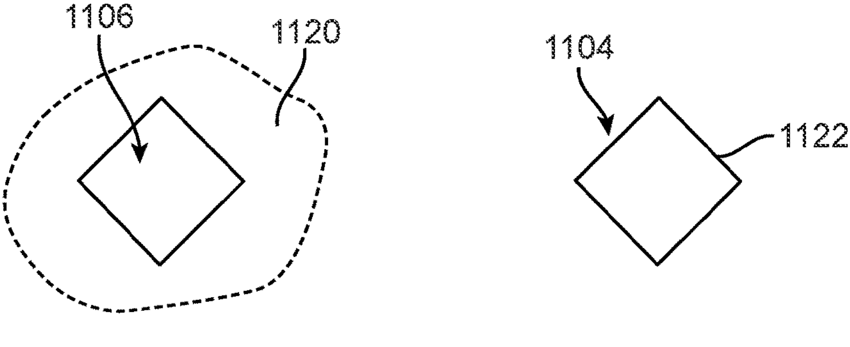
FIG. 19B
FIG. 19C

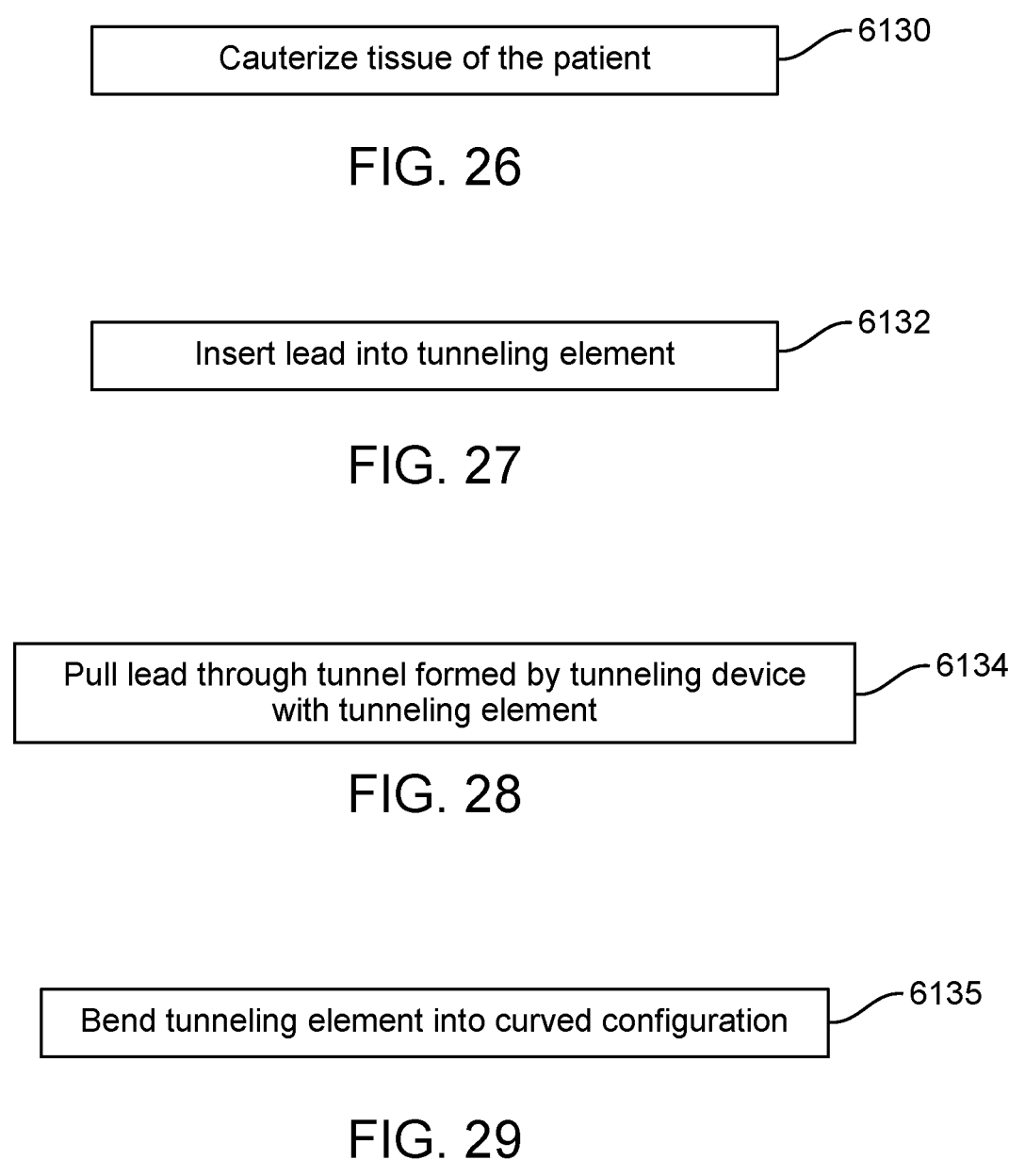

Cauterize tissue of the patient
6130

FIG. 26

Insert lead into tunneling element
6132

FIG. 27

Pull lead through tunnel formed by tunneling device with tunneling element
6134

FIG. 28

Bend tunneling element into curved configuration
6135

FIG. 29

SURGICAL TUNNELING DEVICES AND METHODS

CROSS-REFERENCE TO RELATED APPLICATIONS

This application claims the benefit of the filing date of U.S. Provisional Application Ser. No. 63/477,441, filed Dec. 28, 2022 and entitled "Surgical Tunneling Devices and Methods," the entire teachings of which are incorporated herein by reference.

BACKGROUND

The implantation of some implantable medical devices, such as a lead, may involve first forming a tunnel within a patient's body to provide a path by which the implantable medical device may be advanced into a desired position within the body. In some instances, a tool, which is separate from the implantable medical device, may be used to form the tunnel.

BRIEF DESCRIPTION OF THE DRAWINGS

FIG. 2C is a side view of the example surgical tunneling device of FIGS. 2A-2B in a curved arrangement.

FIG. 3 is a partial, top view of a proximal end of the example surgical tunneling device of FIGS. 2A-2B.

FIG. 4 is a partial, enlarged side view of a distal end of the surgical tunneling device of FIGS. 2A-3 according to an example of the disclosure.

FIGS. 9A-9B illustrate an alternate example tunneling element.

FIG. 10A is an end view of a recess, which can be incorporated into a handle, that can be utilized with the tunneling element of FIGS. 9A-9B according to an example of the disclosure.

FIG. 10B is an end view of another recess, which can be incorporated into a handle, that can be utilized with the tunneling element of FIGS. 9A-9B according to an example of the disclosure.

FIG. 19A is a side view of an alternate example surgical tunneling device having a handle and a tunneling element having a user's hand partially shown in dashed line (the opposing side view of the tunneling device being a mirror image of FIG. 19A in some examples).

FIG. 19B is a partial, bottom view of the handle of FIG. 19A at area A.

FIG. 19C is a cross-sectional view of the tunneling element of FIG. 19A.

FIGS. 24A-29 are block diagrams schematically representing example methods of using surgical tunneling devices of the disclosure.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to devices for diagnosis, therapy, and/or other care of medical conditions throughout the body. At least some examples may comprise implantable devices and/or methods comprising use of implantable devices. In some examples, the implantable medical devices may include a pulse generator.

At least some of the example devices and/or example methods may relate to sleep disordered breathing (SDB) care, which may comprise monitoring, diagnosis, and/or stimulation therapy with an implantable pulse generator.

Aspects of the disclosure include surgical tunneling devices having a handle and a tunneling element, wherein a rotational position of the handle can be maneuvered or rotated with respect to the tunneling element to a different rotational position. The handle may be gripped by a clinician to manipulate the tunneling element and apply torque to the tunneling element to form a pathway within a patient body. Advancing the distal end of the tunneling device subcutaneously through the patient's body may comprise rotating the handle to facilitate directional maneuvering/advancement of the conduit within the patient's body (e.g., among, through, subcutaneous tissues, structures) as forming the pathway. One significant benefit of aspects of the disclosure is that a clinician can adjust the rotational orientation of the handle with respect to the tunneling element as desired throughout a procedure as many or as few times as they desire to achieve the most effective tunneling and ergonomic effect during a tunneling procedure from an incision to a target area (e.g., to an implanted pulse generator or other implanted medical device). Therefore, the degree of adjustment and number of adjustments is customizable.

Figures 1A, 1B, 1C:
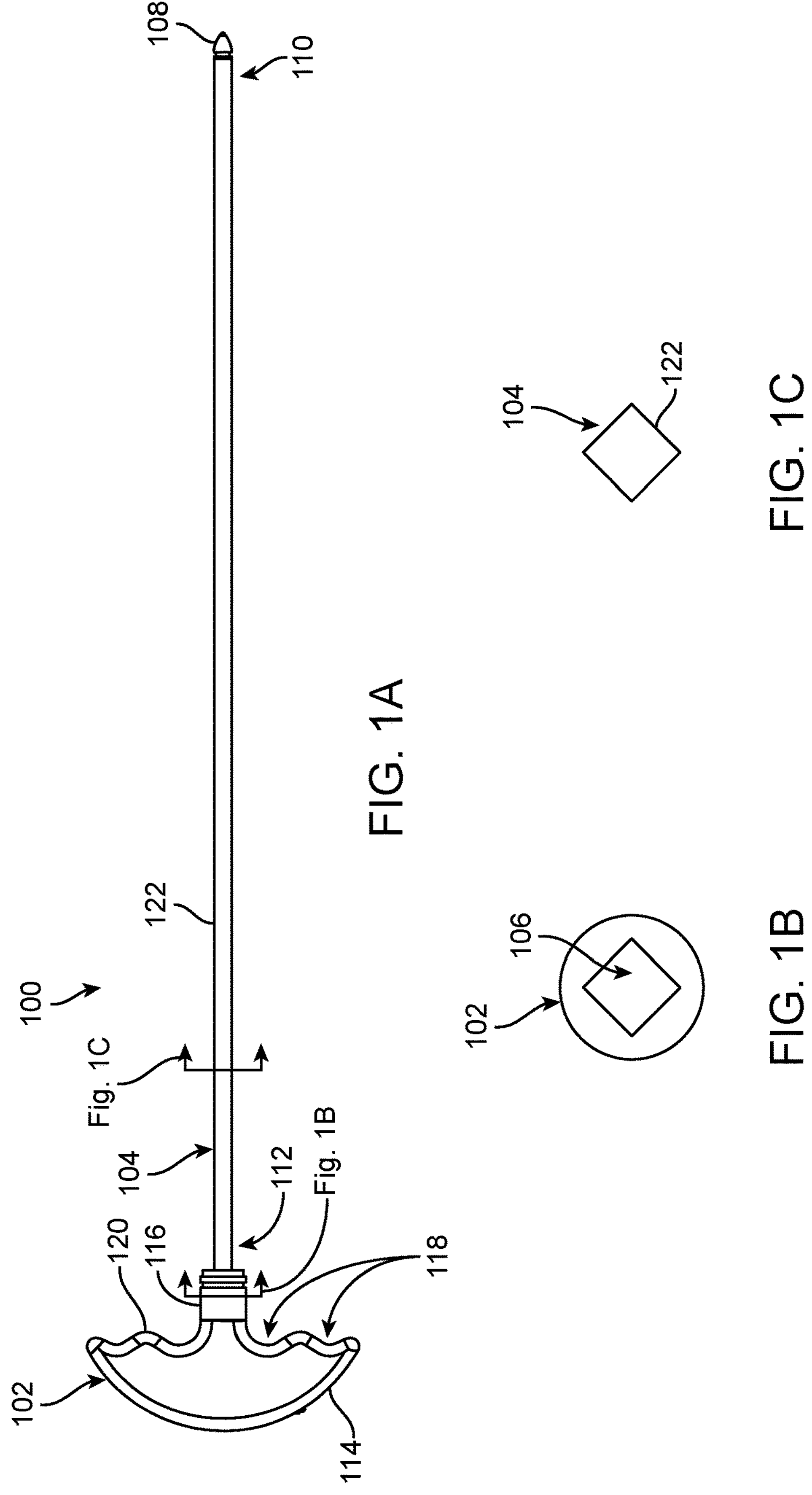
FIG. 1A is a side view of an example surgical tunneling device of the disclosure having a tunneling element connected to a handle.
FIG. 1B is a cross-sectional end view of the handle of FIG. 1A having a recess for receiving the example tunneling element.
FIG. 1C is a cross-sectional view of the example tunneling element of FIG. 1A.

Referring now to FIGS. 1A-1C, which illustrate a surgical (i.e. medical) tunneling device 100, which can otherwise be referred to as a surgical device or simply a "tunneling device". In some examples, the surgical tunneling device 100 is used to form a tunnel in a body of a patient and to further connect a lead to an implantable pulse generator (see also, FIGS. 21-22). In some examples, the lead may be a stimulation lead (see also FIGS. 22 and 23A-23B), a sensor lead, a power transmission lead, or a signal transmission lead. In some examples, the implantable pulse generator is configured to provide electrical stimulation therapy to a nerve or other bodily tissue, receive a sensing parameter, or to transmit power or electrical signals to another region of the body. As shown in FIG. 1A, the tunneling device 100 can include a handle 102 selectively fixable relative to a tunneling element 104, which may sometimes be referred to as "tunneler". In one example, the tunneling element 104 is solid but in other examples, the tunneling element can include a channel or can otherwise not be solid. The tunneling element 104 may be malleable and include an atraumatic distal tip 108 at a distal end 110 of the tunneling element to assist in forming a pathway in a body. In some examples, the tunneling element 104 has a smooth outer surface, void of sharp corners or portions that could snag during a procedure. In one example, the distal tip 108 is closed. In one example, the handle 102 includes a recess 106 having a shape corresponding to a cross-sectional shape of a proximal end 112 of the tunneling element 104 (see, e.g., FIGS. 1B-1C). In some examples, the handle 102 is symmetric as viewed from one or more angles but in other examples, the handle 102 is non-symmetric as viewed from one or more angles (see also, FIGS. 19A-20) and related disclosure. In the non-limiting illustrated example, the recess 106 and the proximal end 112 of the tunneling element 104 have corresponding square cross-sections/shapes. In this way, a proximal end 112 of the tunneling element 104 can be inserted into the recess 106 at a plurality of rotational positions (e.g., four rotational positions). In various non-limiting examples, the cross-sectional shape of the recess 106 and the proximal end 112 of the tunneling element 104 may be non-circular, symmetrical, and/or polygonal. In various examples, the tunneling element 104 can be engaged with the recess at a plurality, fixed or finite number of rotational positions. In non-limiting examples, the number of rotational positions available is equal to or less than 12, equal to or less than 8, or equal to or less than 6. In some examples, the handle 102 can be selectable engaged into different rotational positions that are in increments ranging from 10 to 120 degrees. In some examples, the increments are equally spaced but in other examples they may not be.

In one example, the tunneling device 100 has a locked arrangement in which a rotational position of the handle 102 is fixed with respect to the tunneling element 104 and the tunneling device 100 further includes an unlocked arrangement in which the rotational position of the handle 102 is adjustable with respect to the tunneling element 104. In various examples, in the locked arrangement, the tunneling element 104 is rotationally locked with respect to the handle 102. In various examples, when the tunneling element 104 is engaged with the handle 102, the tunneling element 104 is configured to form a locking engagement with the handle 102 at a location distal to a grip portion 114 of the handle. In various examples, the tunneling element 104 can be formed via stamping, laser welding, cutting (laser or otherwise), over molding, snap fitting, and a combination thereof.

In some examples, the handle 102 includes the grip portion 114 and a stem portion 116 extending from the grip portion 114. In some examples, the grip portion 114 can include a plurality of indentations 118 (generally referenced) for a user's fingers to be positioned while gripping the handle. In one example, the indentions 118 are positioned on a bottom surface 120 of the grip portion 114. In some examples, the recess 106 is positioned in the stem portion 116.

In contrast to at least some later described examples, the tunneling element 104 of FIGS. 1A-1C may omit a separate core that would be otherwise removably insertable within/through the tunneling element. In another example, the handle 102 may be screwed onto or compression fitted to the proximal end 112 of the tunneling element 104.

In some examples, the distal tip 108 may be removably securable to a body 122 of tunneling element 104 while in some examples, the distal tip 108 may be permanently secured to a distal end 110 of the body 122 of the tunneling element 104.

Referring now in addition to FIGS. 2A-6C in some examples, a surgical or medical tunneling device 200 includes a handle 202 and a tunneling element 104, the handle 202 being selectively fixable into different rotational positions relative to the tunneling element 204. In some examples, the tunneling device 200 of FIGS. 2A-6C may comprise at least some of substantially the same features and attributes of the examples of FIGS. 1A-1C.

Figures 2A, 2B:
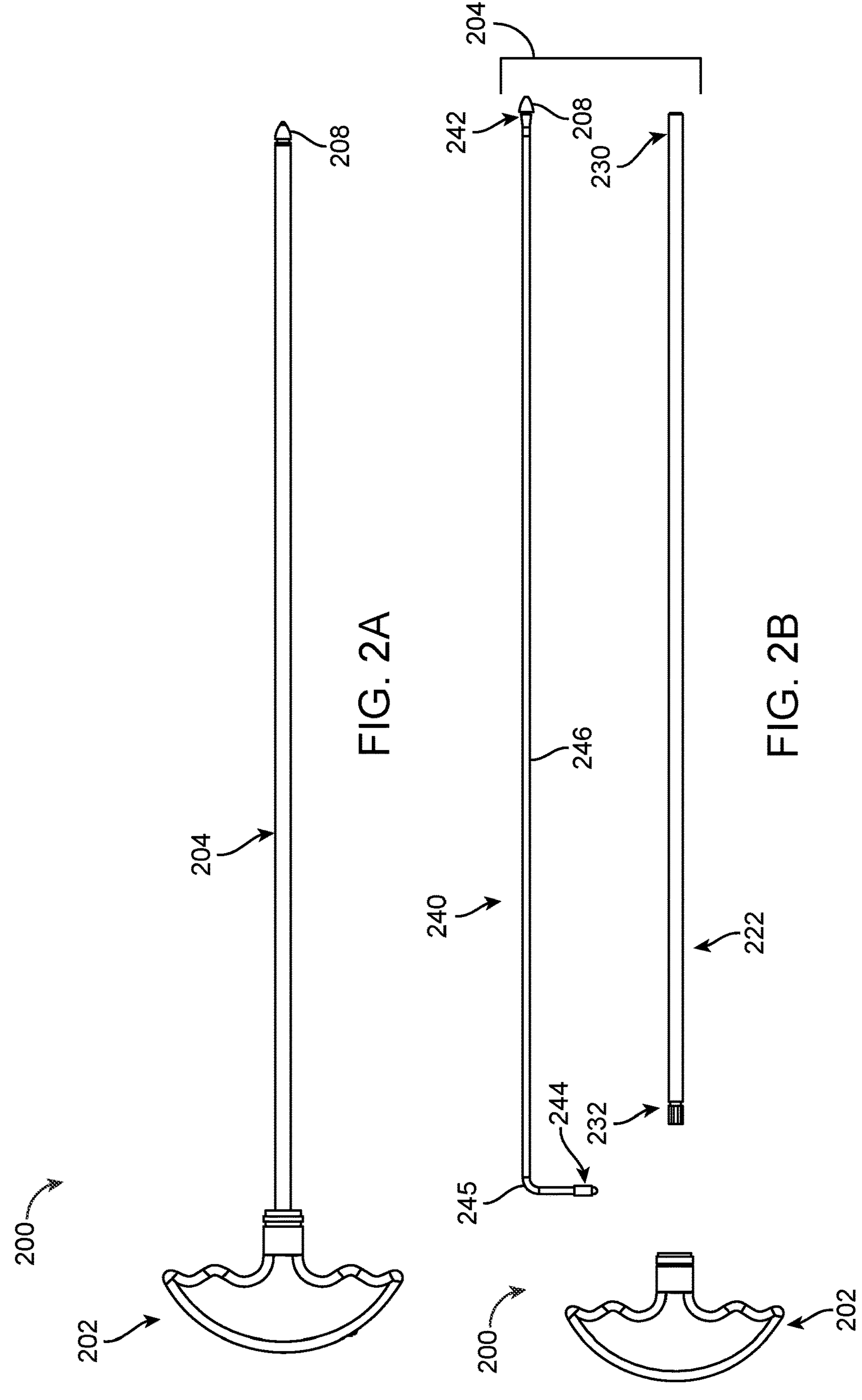
FIG. 2A is a side view of an alternate example surgical tunneling device.
FIG. 2B is an exploded view of the example surgical tunneling device of FIG. 2A.
Figure 5:
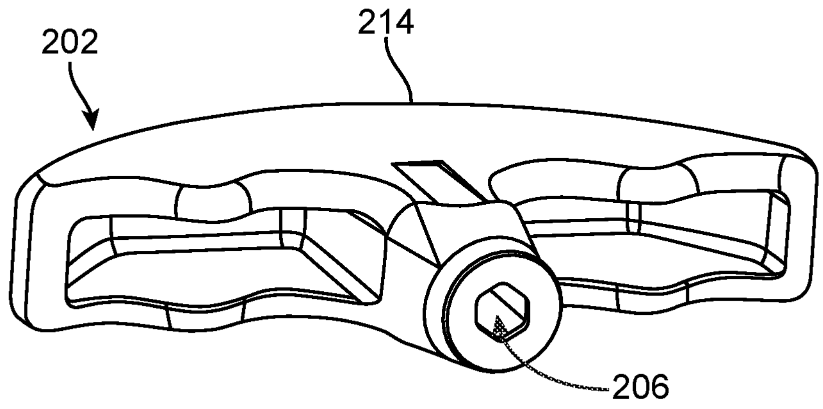
FIG. 5 is a perspective view of a handle of the surgical tunneling device of FIGS. 2A-2C according to an example of the disclosure.

In these examples, the tunneling element 204 includes a conduit 222, 222', 222" (which may otherwise be described as a body or sheath) defining a channel 224, 224', 224" (FIGS. 6A, 6B, 6C) in which a core 240 of the tunneling element 204 can slide and be at least partially housed in the assembled state of FIG. 2A. Throughout the description of these examples, if one of conduits 222, 222', or 222" is referenced, including at least one of its components, it is recognized that another suitable conduit (e.g., 222, 222', or 222"), including at least one of its components, could be substituted therefor. In some examples, the conduit 222, 222', 222" is tubular. In one example, the channel 224, 224', 224" extends through an entire length of the conduit 222, 222', 222" so that the core 240 can extend through both distal ends 230, 230', 230" and proximal ends 232, 232', 232" of the conduit 222, 222', 222". In some examples, the channel has a cross-sectional shape that is circular, non-circular (e.g., polygonal), symmetrical, or non-symmetrical. In one example, illustrated in FIGS. 6A, 6B, the cross-sectional shape of the channel 224, 224' is polygonal (e.g., hexagonal). In another example, illustrated in FIG. 6C, the cross-sectional shape of the channel 224" is circular. It is recognized that the cross-sectional shape of the channel could be the same or different along a length of the channel and could be any suitable cross-sectional shape.

Figure 6A:
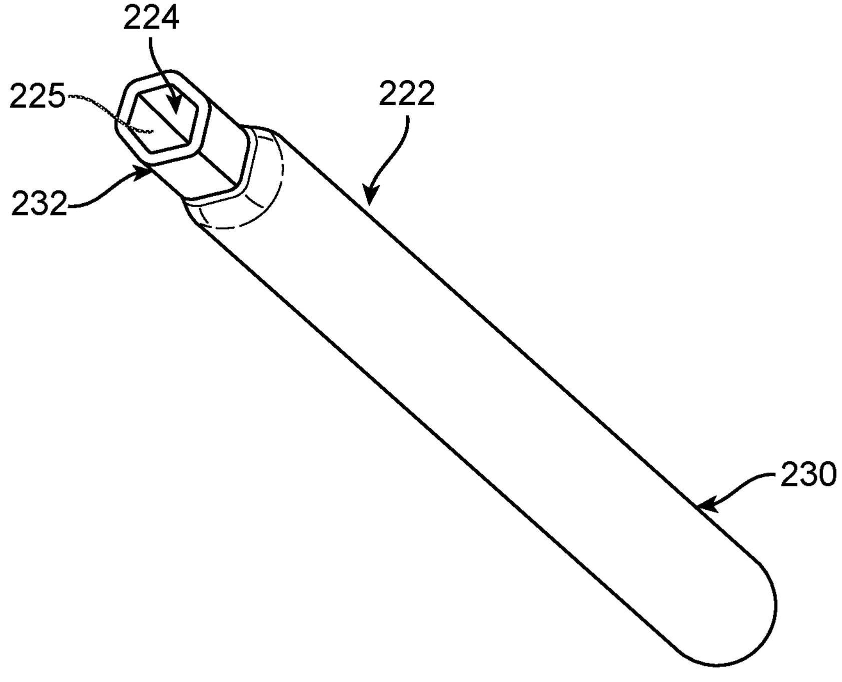
FIG. 6A is a perspective view of an example tunneling element of the surgical tunneling device of FIGS. 2A-2C.
Figure 6B:
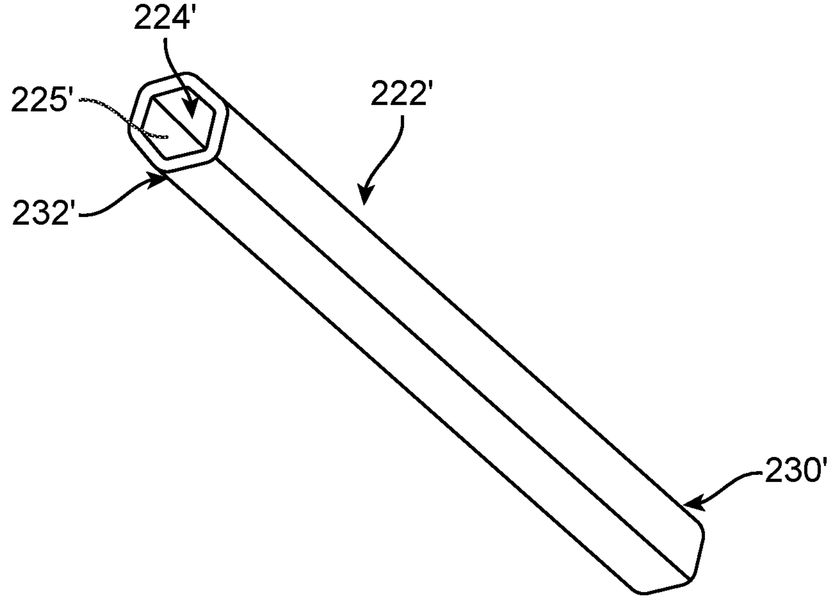
FIG. 6B is a perspective view of an alternate example tunneling element of the surgical tunneling device of FIGS. 2A-2C.
Figure 6C:
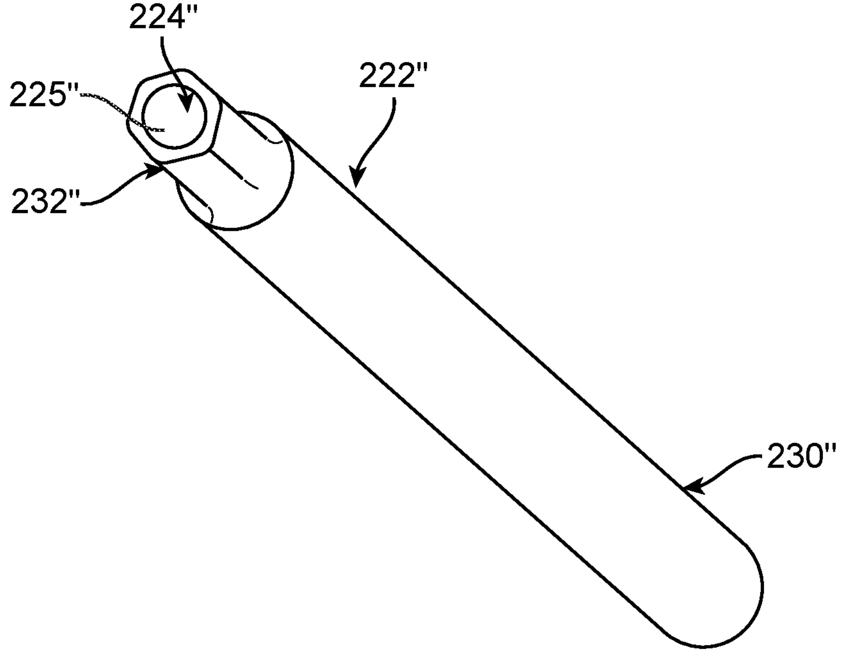
FIG. 6C is a perspective view of another alternative example tunneling element of the surgical tunneling device of FIGS. 2A-2C.

The handle 202 may include a recess 206 (FIG. 5) having a cross-sectional shape that corresponds to a cross-sectional shape of an outer surface portion of conduit 222, 222', 222" so that the conduit 222, 222', 222" can be used to engage the handle 202 in the locked arrangement. In various non-limiting examples, the cross-sectional shape of the recess 206 and an outer surface portion of the conduit 222, 222', 222" may be non-circular, symmetrical, and/or polygonal (e.g., hexagonal). In some examples, at least the proximal end 232 of the outer surface portion of conduit 222, 222', 222" includes a cross-sectional shape corresponding with the cross-sectional shape of the recess 206 and a remaining outer surface portion of the conduit 222, 222', 222" can have any suitable shape, which can be the same as or different than the cross-sectional shape of the recess 206. FIGS. 6A and 6C illustrate the proximal ends 232, 232" of conduit 222, 222" including outer surface portions having cross-sectional shapes corresponding with that of the recess 206. FIG. 6B illustrates an entire length of the outer surface portion of conduit 222' having a cross-sectional shape corresponding with that of the recess 206. It is recognized that the cross-sectional shape of at least the proximal end can extend into an intermediate portion of the conduit positioned between the distal and proximal ends and any suitable transitional configuration between cross-sectional shapes can be used. With at least the proximal end of the conduit including an outer surface portion having a cross-sectional shape corresponding with that of the recess 206, the conduit 222, 222', 222" can be engaged with the recess 206 at a plurality, fixed or finite number of rotational positions. In various non-limiting examples, the number of rotational positions is equal to or less than 12, equal to or less than 8, equal to or less than 6. In some examples, the handle 202 can be selectably engageable in different rotational positions that are in increments ranging from 10 to 120 degrees. In some examples, the increments are equally spaced but in other examples they may not be.

The conduit 222, 222', 222" may, in some examples, be made of a malleable material. In some examples, a distal tip 208 of the core 240 has a greater rigidity than the conduit 222, 222', 222" (e.g., at least 25% more rigid). In one example, the conduit 222, 222', 222" is configured to limit rotational movement of the core 240 when the core 240 is at least partially positioned within the channel 224, 224', 224". In various examples, this is accomplished by configuring the core 240 and the conduit 222, 222', 222" to have a slidably close, friction fit. As can be seen in FIG. 2B, in some examples, the core 240 has a length that is greater than a length of the conduit 222. For example, once removably inserted, the core 240 may extend out of a distal end 230 of the conduit 222 and having the domed distal tip 208 to provide an atraumatic contact surface during a tunneling procedure. In various examples, the core 240 has a distal end 242, a proximal end 244 and a body portion 246 between the distal and proximal ends. In the illustrated example, the proximal end 244 has a bent portion 245. In one example, the bent portion 245 forms an angle of about 90 degrees (+/−20 degrees), including when the tunneling device is in the assembled arrangement of FIG. 2A. In some examples, a distal end 242 of the core 240 has a greatest outer diameter that is larger than an inner diameter of the channel 224 of the conduit 222.

As perhaps best shown in FIG. 3, in various examples, the handle 202 is configured to engage and retain the core 240 of the tunneling element 204. In one example, the core 240 extends through the recess 206 to retaining members 250 positioned within a channel 252 formed outside of the recess 206, within a handle grip portion 214, opposite a bottom surface 220 of the grip portion 214 and also opposite a stem portion 216 and in which the recess 206 is formed. In FIG. 3, the retaining members 250 maintain the core in a locked position in where the core 240 cannot move longitudinally with respect to the conduit 222. The retaining member(s) 250 can, in some examples, be configured to releasably retain the core 240 in the locked position via a force fit or the like.

As indicated above, in some examples, the core 240 and conduit 222 are configured to have a friction fit. Therefore, it may be desirable, in some examples, for the core 240 and/or channel 224 to include a lubricous coating 241, 225, respectively, so that the core 240 can be inserted within and withdrawn from the channel 224 of the conduit 222, as desired. In another example, an outer surface of the core 240 and/or distal tip 208 include a lubricous coating to reduce friction during a tunneling process.

It is to be understood that all other aspects of the tunneling device 200 of FIG. 2 can be similar or identical to that of FIGS. 1A-1C and that other features of other embodiments disclosed herein may also be incorporated into the embodiment of FIGS. 2A-6C.

Similar to other embodiments of the disclosure, the tunneling device 200 has a locked arrangement and an unlocked arrangement. In one example of the locked arrangement, the handle 202 is engaged with the tunneling element 204 and in one example of the unlocked arrangement, the handle 202 is disconnected from the conduit 222. In one example of the locked arrangement, the handle 202 is engaged with both the conduit 222 and the core 240. In various examples, when the tunneling element 204 is connected to or engaged with the handle 202, the core 240 of the tunneling element 204 is configured to form a locking engagement with the handle 202 at a location distal to the grip portion 214. In one example, the recess 206 corresponds to a cross-sectional shape of the core 240 such that rotational movement or torqueing of the handle 202 is correspondingly transferred to the conduit 222 when the tunneling device 200 is in the locked arrangement.

Figure 7:
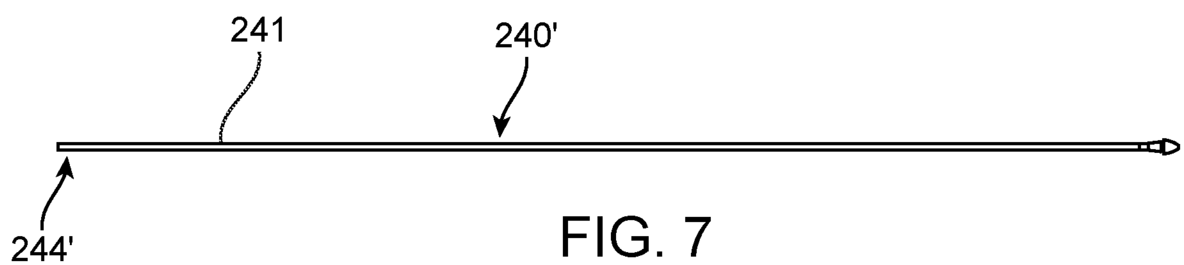
FIG. 7 is a side view of an example core configuration.

Referring now in addition to FIG. 7, in some examples, a core 240' has a linear proximal end 244' as compared to the proximal end 244 of the embodiment of FIG. 2B in which the proximal end has a bend.

Figure 8:
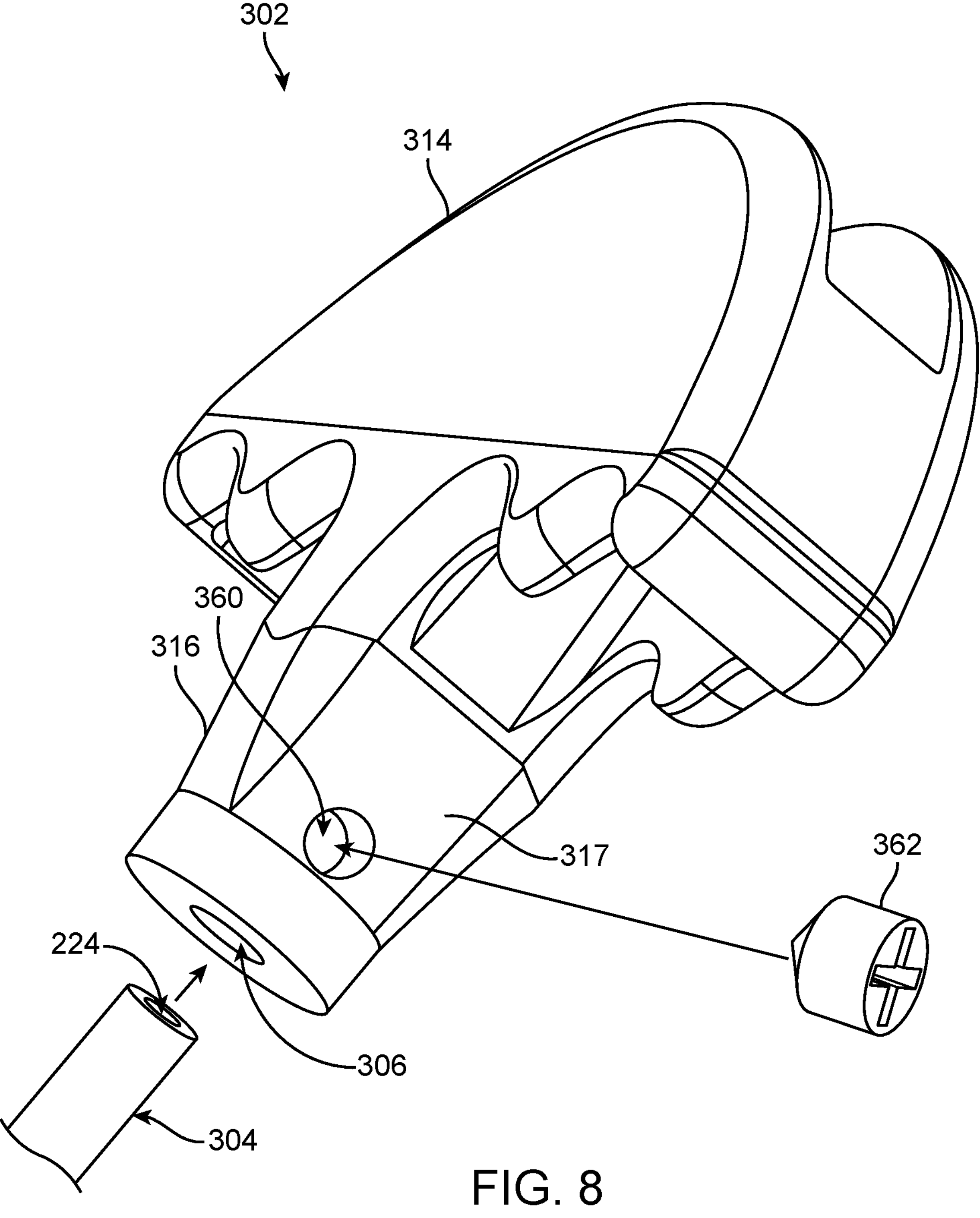
FIG. 8 is a perspective view of an alternate example handle.

Referring now in addition to FIG. 8, which illustrates an alternate example handle 302 that can be utilized in any of the embodiments of the disclosure. In some examples, the handle 302 of FIG. 8 may comprise at least some of substantially the same features and attributes of the prior examples. In the illustrated example, the handle 302 includes a grip portion 314 and a stem portion 316 having a recess 306 to receive a tunneling element 304. In this example, the stem portion 316 includes a side aperture 360 extending through a wall 317 of the stem portion 316 in which a lock 362 can be inserted. In one example, the lock 362 is a screw or the like. In an unlocked arrangement, the lock 362 is removed or loosened from the side aperture 360 so that the tunneling element can be withdrawn from the recess 306 and a rotational position of the handle 302 can be adjusted with respect to the tunneling element 304. In a locked arrangement, the tunneling element is partially positioned within the recess 306 and the lock 362 is inserted within the side aperture 360 such that the lock 362 engages the tunneling element, maintaining a rotational alignment of the tunneling element with respect to the handle 302. To further or re-adjust the rotational alignment of the tunneling element with respect to the handle 302, the lock 362 is withdrawn from the side aperture 360, the tunneling element is rotated within the recess 306 a desired degree and then the lock 362 is reinserted within the side aperture 360 to re-engage the tunneling element. In another example, the tunneling element can be withdrawn from the recess 306, rotated to a desired position and then reinserted within the recess 306 before the lock 362 is reinserted within the side aperture 360 to engage the tunneling element and maintain it in its rotational position with respect to the handle 302. As the lock 362 maintains a rotational orientation of a tunneling element in this example, the tunneling element 304 can optionally have a circular cross-section, which may or may not include a channel 324. In all other respects, the handle 302 and tunneling element 304 can be similarly configured to and include any other features of any other handle of the disclosure.

Referring now in addition to FIGS. 9A-10B, which illustrate an alternate example tunneling element 404. In some examples, the tunneling element 404 may comprise at least some of substantially the same features and attributes of the prior examples. In this example, the tunneling element 404 includes a conduit 422 (or body) having a distal end 432 and a proximal end 434. The conduit 422 can define a channel 424 to receive a distal end of a core (e.g., core 240 similar to the embodiment of FIGS. 2A-2C, 7) or the conduit 422 can be replaced with a tunneling element similar to that of FIGS. 1A-1B. In this example, the proximal end 434 includes a mating element 436 (otherwise referred to a key) for inserting within a corresponding mating element 406, 406' (e.g., correspondingly shaped recess) of a handle 402, 402' to facilitate transition between a locked arrangement and an unlocked arrangement. In this example, the key 436 and recess 406, 406' are configured to having a mating, or corresponding, relation. Additionally, in this example, the key 436 and recess 406, 406' are configured such to prevent rotation of the tunneling element with respect to the handle 402, 402' (FIGS. 10A-10B) when the key 436 is operatively inserted within the recess 406 in the locked arrangement. In this way, the key 436 may have a non-circular, symmetrical, and/or polygonal cross-section. In one example, the recess 406 is configured such that the key 436 can be engaged with the recess 406 at a plurality of rotational positions. As shown in FIGS. 10A-10B, various non-limiting examples include the key 436 having a teardrop shaped cross-section (i.e. ovate shaped) and the mating element/recess 406, 406' having a one or more apex sections 407*b* so that the key 436 can be inserted into the recess 406 at two rotational positions (e.g., at least two positions 90 degrees more or less apart, at least three positions at 120 degrees more or less apart). In one example, the key 436 includes a circular or other-shaped section 337*a* from which a protrusion 437*b* extends. The protrusion 437*b* being configured to fit within each apex section 407, 407' and, in one example, having a shape corresponding to the apex section 407, 407'. In the illustrative example of FIG. 10A, the key 436 can be engaged with the recess 406 in three rotational positions at apex sections 407 with respect to the handle 402, each position 120 degrees apart. In the illustrative example of FIG. 10B, the key 436 can be engaged with recess 406' in two rotational positions with respect to handle 402', the two positions (apex sections 407') spaced 90 degrees. It will be understood that the number of rotational positions available can vary and the present disclosure is not intended to be limited to one, two, three or any specific number. It will be further understood that the number of positions available will affect the number of rotational angles the tunneling element can be adjusted with respect to the handle (and vice versa). It will even further be understood that each rotational position available (as defined by the recess) can be either uniformly spaced about a circumference of the recess or could be unequally spaced about the circumference of the recess.

In one example, as best shown in FIG. 9A, the proximal end 434 of the conduit 422 has a greater widest diameter as compared to a widest diameter of the distal end 432 of the conduit 422. It is further envisioned that, in some examples, the conduit 422 may be an integrally formed component. It will be understood that the conduit of FIGS. 9A-9B can otherwise be configured and operate similarly to other conduit of the disclosure and can be used with a handle including any of the features disclosed herein as long as the handle has a corresponding recess for the particular key configuration of the respective conduit.

Figure 11:
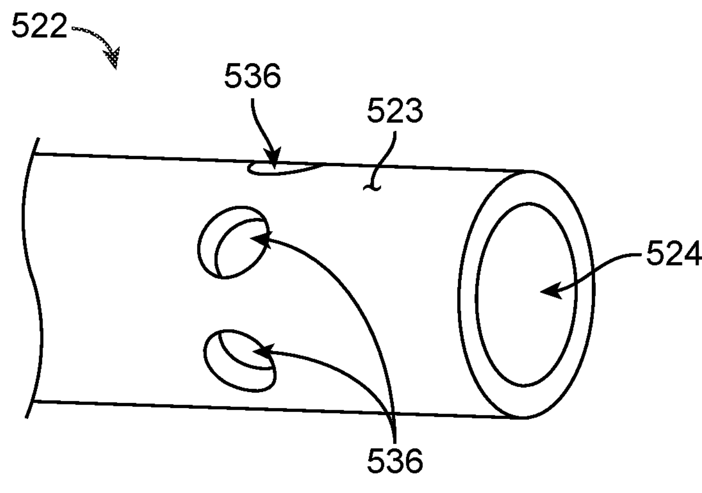
FIG. 11 is a partial, perspective view of a proximal end of an alternate tunneling element according to an example of the disclosure.
Figure 12:
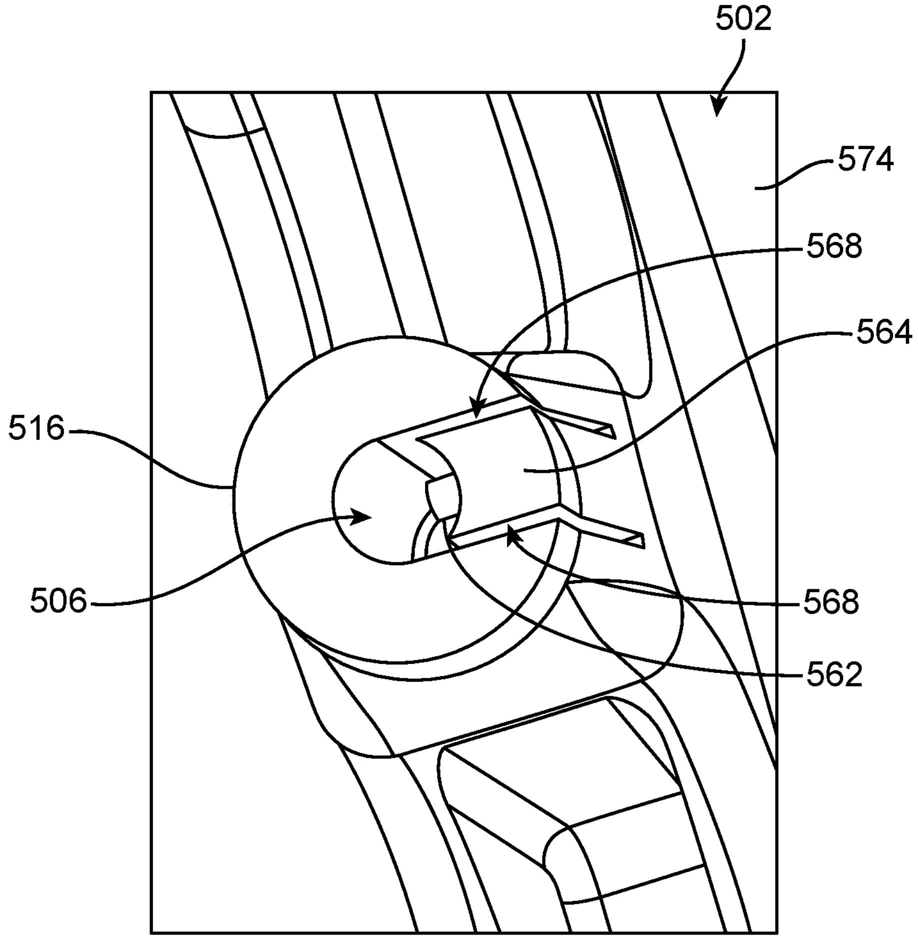
FIG. 12 is a partial, bottom view of a handle that can be utilized with the tunneling element of FIG. 9 according to an example of the disclosure.

Referring now in addition to FIGS. 11-12, which illustrate yet another conduit 522 (FIG. 11) and handle 502 (FIG. 12) that can be used in examples of the disclosure. In some examples, the conduit 522 and handle 502 may comprise at least some of substantially the same features and attributes of the prior examples. In some examples, where a core (e.g., core 140) is not utilized, the conduit 522 may constitute a "tunneling element" or at least part of a tunneling element similar to the embodiment of FIG. 1A. In other examples where the conduit 522 is not all or partially hollow, the conduit may alternately be referred to as a "body". In this example, the conduit 522 includes a plurality of mating elements 536 within or applied to its outer surface 523, about at least a portion of a circumference of the conduit 522. The illustrated example includes the mating elements 536 being a plurality of apertures extending through the entire thickness or wall at least partially defining the conduit 522 and equidistantly spaced about the entire circumference of the conduit 522. In this way, each of the plurality of apertures (i.e. mating elements) 536 intersect with a channel 524 of the conduit 522 that extends a full length of the conduit 522 in one example. In some examples, the mating elements 536 can be apertures, pockets or indents. With such mating elements 536, a lock 562 of the handle 502 can engage the conduit 522 at a finite number of positions about the outer surface 523 of the conduit 522 when the conduit 522 is inserted within a recess 506 adjacent the lock 562. In one example, the lock 562 resembles a pin. In the illustrated example, the finite number of positions is a number greater than one. In other examples, the recesses may extend through only part of the conduit 522 and may not intersect with the channel 524 of the conduit 522. As in this example the conduit 522 is configured to be received within the recess 506, the recess 506 and conduit 522 may have corresponding cross-sectional shapes (e.g., circular).

In various embodiments, the handle 502 includes a grip portion 514 and a stem portion 516 in which the recess 506 may be located. In one example, the lock 562 protrudes into the recess 506 and may define at least a portion of the recess 506. In one example, the lock 562 is configured to engage the conduit 522 in a locked arrangement in which a rotational position of the conduit 522 is fixed with respect to the handle 502. In some examples, the conduit 522 is rotationally aligned to a desired position with respect to the handle 502 and then the conduit 522 is inserted within the recess 506. In various examples, the lock 562 may be biased to flex inwardly with respect to the recess 506. In such examples, when the conduit 522 is inserted within the recess 506, the conduit 522 is sized such that it pushes the lock 562 outwardly against its bias to allow the conduit 522 to pass in a proximal direction until one of the mating elements 536 passes by the lock 562 so that the lock 562 pops into the respective mating element 536 to maintain both a rotational and longitudinal position of the conduit 522 with respect to the handle 502. Biasing can be achieved, for example, with a spring, material selection or other structural configuration of the lock 562 and other surrounding components of the handle 502. In the illustrated example, the lock 562 is secured to a support block 564. In one example, a gap 568 is positioned on each side of the support block 564, which, at least in part, allows the support block 564 and lock 562 to flex with respect to the stem portion 516 and recess 506. As one of the recesses moves adjacent the lock 562, the biased lock 562 is allowed to move inwardly to its biased position (FIG. 12), to extend within the recess 506 to engage the conduit 522 in a locked arrangement in which a rotational position of the conduit 522 is locked with respect to the handle 502. To transition to an unlocked arrangement in which the rotational position of the conduit 522 with respect to the handle 502 can be adjusted. In some examples, to disengage the lock 562 from the aperture 536, a tool may be used to pry or deflect the arm 564. Alternatively, arm 564 may comprise a feature to allow the user to pull or deflect the arm 564 away from the conduit 522. Alternatively, the detent 562 may comprise a ball detent or spring loaded detent, where it does not rotate under a moderate amount of torque, but can be disengaged and rotated if torque over a certain threshold is applied. It will be understood that the conduit 522 and handle 502 of FIGS. 11-12 can otherwise be configured and operate similarly to other conduits and handles, respectively, of the present disclosure and can be incorporated into any of the devices disclosed herein. Except as explicitly stated, the conduit/tunneling element and handle of FIGS. 11-12 can additionally include alternate features and elements disclosed herein with respect to other conduit/tunneling elements and handles.

Figure 13:
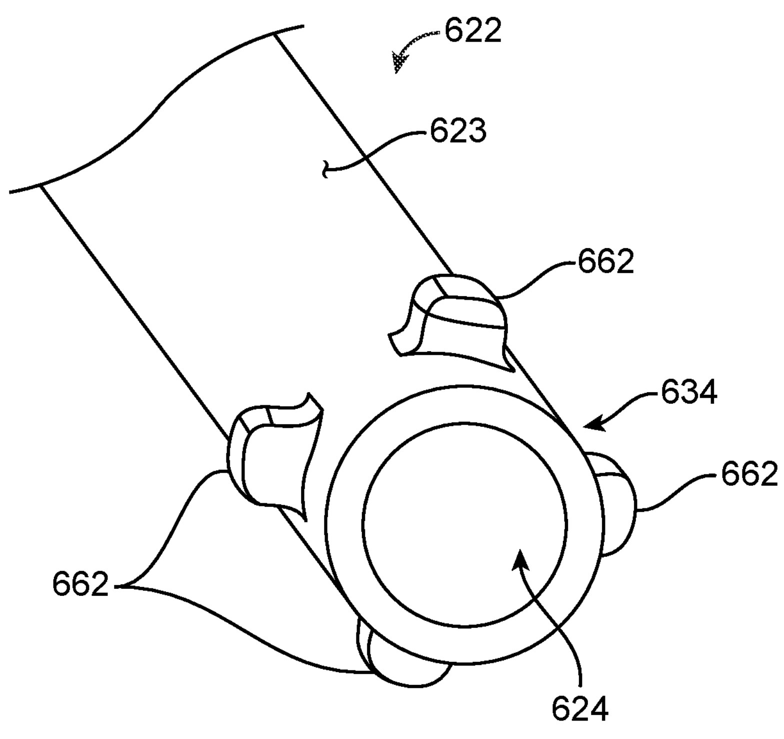
FIG. 13 is a partial, perspective view of a proximal end of an alternate tunneling element according to an example of the disclosure.
Figure 14:
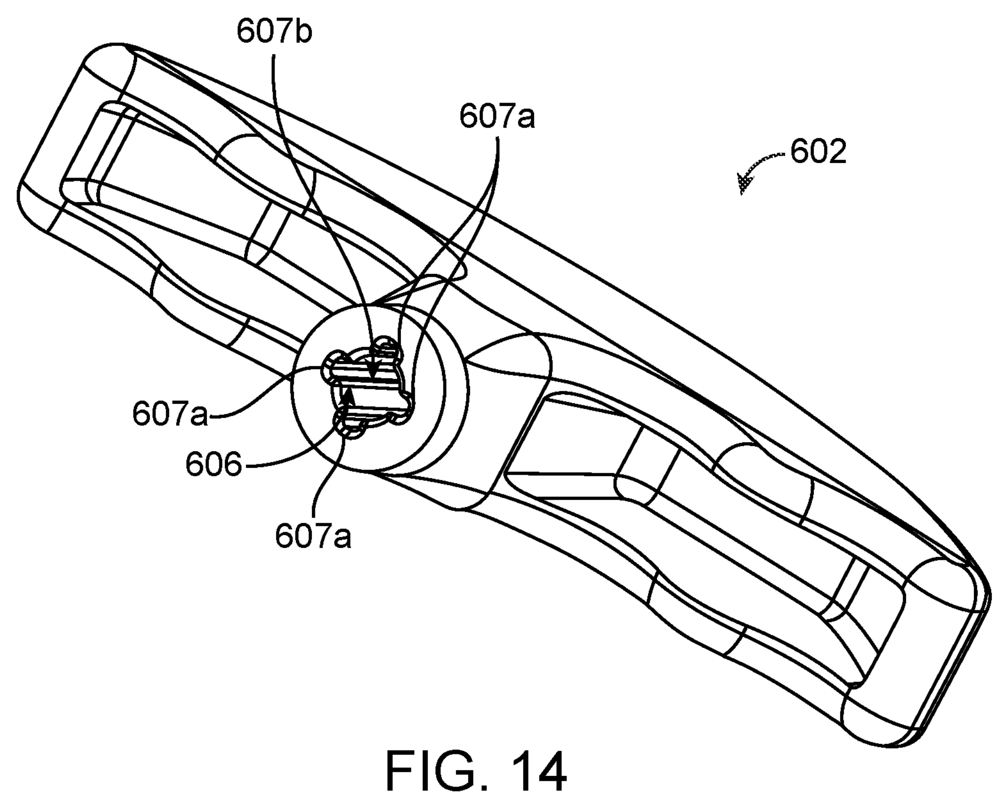
FIG. 14 is a bottom view of a handle that can be utilized with the tunneling element of FIG. 13 according to an example of the disclosure.

Referring now in addition to FIGS. 13-14, which illustrate yet another conduit 622 (FIG. 13) and handle 602 (FIG. 14) that can be utilized in examples of the disclosure. In some examples, the conduit 622 and handle 602 may comprise at least some of substantially the same features and attributes of the prior examples. In this example, the conduit 622 and handle 602 include corresponding mating elements 662, **607*a* to facilitate transition between the locked and unlocked arrangements. In one example, a proximal end 634 of the conduit 622 includes the plurality of mating elements 662 about a circumference of its outer surface 623, which can include protrusions in various examples. The number of protrusions or mating elements 662 and can be selected to designate the number of rotational position options the conduit 622 can be arranged with respect to the handle 602. The handle 602 includes a recess 606 configured to receive the proximal end 634 of the conduit 622, including the mating elements 662. In one example, the corresponding mating elements 607*a* can be considered part of the recess 606. As with prior embodiments, the mating elements 662, 607*a* are configured such that when in the locked arrangement, the conduit 622 is within/engaged with the recess 506 and rotational movement of the conduit 622 with respect to the handle 602 is locked so that the handle 602 can be torqued during a tunneling procedure or the like. In the non-limiting illustrated example, the recess 606 includes a central section 707*b* having a plurality of (e.g., four) additional channels 707*a* equally spaced and extending radially outward about a circumference of the central section 707*b*. In some examples, the conduit 622 is configured to be longitudinally and rotationally locked in position with respect to the handle 602 when the conduit 622 is engaged with the handle 602 in the locked arrangement. It will be understood that the conduit 622 and handle 602 of FIGS. 13-14 can otherwise be configured and operate similarly to other conduits and handles, respectively, of the present disclosure and can be incorporated into any of the devices disclosed herein. For example, the conduit 522 need not include a central channel 424 but could be all or at least partially solid. Therefore, the conduit 622 of FIG. 13 can be considered the tunneling element in embodiments where a core is not utilized. Except as explicitly stated, the conduit/tunneling element and handle of FIGS. 13-14** can additionally include alternate features and elements disclosed herein with respect to other conduit/tunneling elements and handles.

Figure 15:
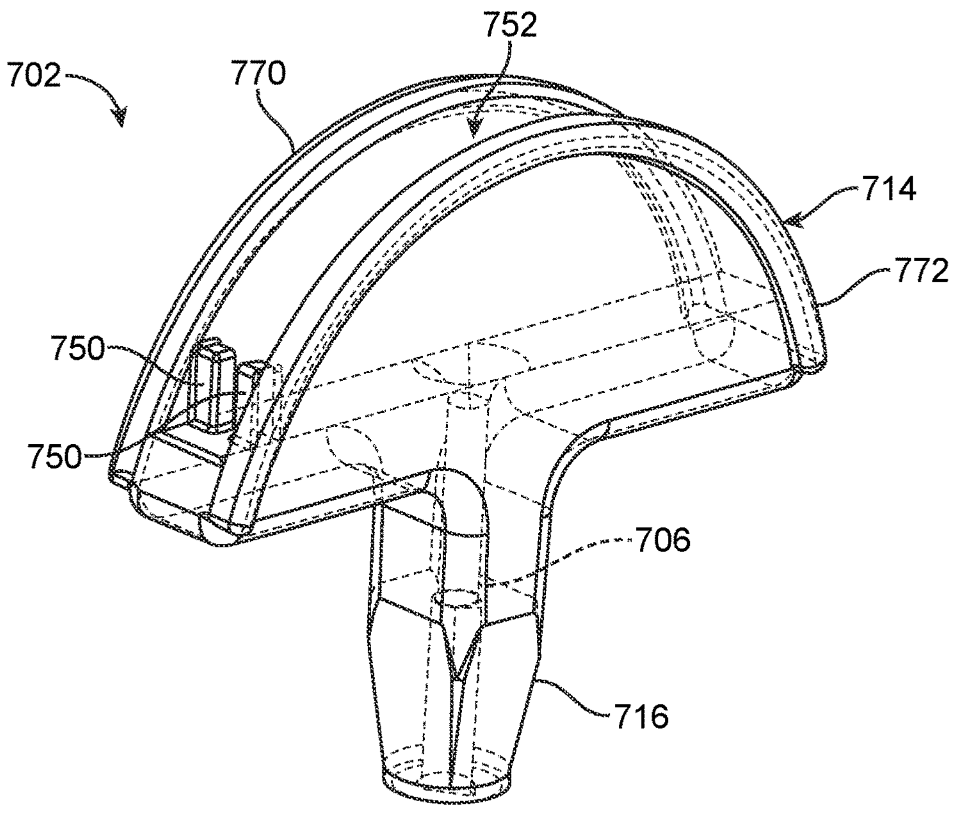
FIGS. 15-18B are perspective views of alternate example handles of the disclosure.

As indicated previously, handles of the disclosure can take many configurations. Referring now in addition to FIG. 15, in one example, a handle 702 can include a grip portion 714 and a stem portion 716. In some examples, the handle 702 of FIG. 15 may comprise at least some of substantially the same features and attributes of the prior examples. The handle 702 is configured to receive a tunneling element (e.g., tunneling element 204) and selectively maintain the tunneling element in any manner within the scope of the disclosure in a locked and unlocked arrangement. In one example, the grip portion 714 includes first and second faces 770, 772, separated from a channel 752 that may extend all or a part of an entire length of the first and second faces 770, 772 (i.e. from one end of the grip to the other). In various examples, the handle 702 can be configured to retain a core (e.g., core 240). In various embodiments, the channel 752 intersects recess 706. In some examples, similar to the embodiment of FIG. 3), one or more retaining members 750 can be provided within the channel 752 to selectively retain the core via friction fit or the like in a locked position. In some examples, the first and second faces 770, 772 can be arranged parallel to each other. In various examples, one or more faces 770, 772 can be semi-circular in shape or identical in shape. The handle 702 of FIG. 15 can otherwise include features and components of any other handle of the disclosure and can be used in any of the devices and methods of the disclosure.

Figure 16:
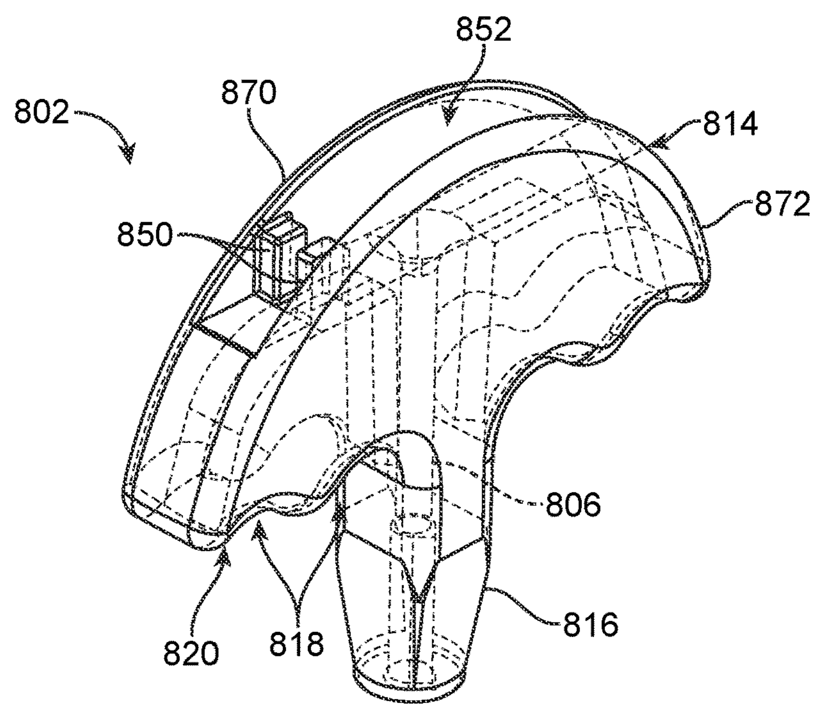

Referring now in addition to FIG. 16, in one example, a handle 802 can include a grip portion 814 and a stem portion 816. In some examples, the handle 802 of FIG. 16 may comprise at least some of substantially the same features and attributes of the prior examples. As with various previously disclosed embodiments, the handle 802 includes a recess 806 configured to receive a tunneling element (e.g., tunneling element 204) and selectively maintain the tunneling element in any manner within the scope of the disclosure in a locked and unlocked arrangement. In one example, the grip portion 814 includes first and second faces 870, 872, separated from a channel 852 that may extend a partial length of the first and second faces 870, 872. In various examples, the handle 804 can be configured to retain a core (e.g., core 240). In some examples, similar to the embodiment of FIGS. 3 and 15), one or more retaining members 850 can be provided within the channel 852 to selectively retain the core via friction fit or the like in a locked position. In one example, the first and second faces 870, 872 can be parallel to each other. In some examples, one or more faces be semi-circular in shape or identical in shape. In this example, a bottom 820 of the grip portion 814, adjacent the stem portion 816, includes a plurality of indentations 818

(generally referenced) to assist a user's grip of the handle 802. The handle 802 and individual handle features of FIG. 16 can otherwise include features and components of any other handle of the disclosure and can be incorporated into any of the devices and methods of the disclosure.

Figure 17:
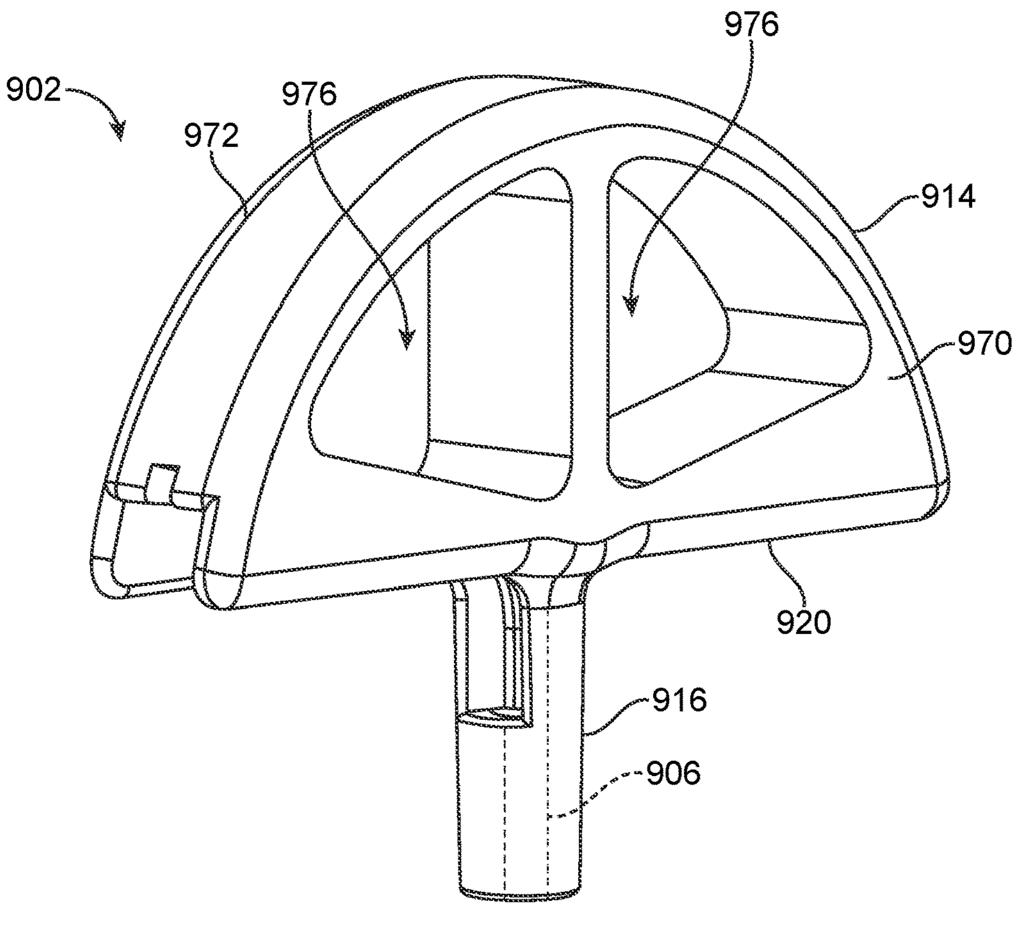

Referring now in addition to FIG. 17, which illustrates another example handle 902 configuration, the handle having a grip portion 914 and a stem portion 916. In some examples, the handle 902 of FIG. 17 may comprise at least some of substantially the same features and attributes of the prior examples. In this example, the grip portion 914 includes first and second faces 970, 972 through which one or more openings 976 extend from the first face 970 to the second face 972. In one example, the fingers may be configured to permit a user to loop one or more of their fingers though one or more openings 976 to achieve greater control and torque during a tunneling procedure of the disclosure. In one example, each opening can define a plane that is perpendicular to a bottom 920 of the grip portion 914. In various examples, the handle 902 can be configured to retain a tunneling element (e.g., tunneling element 204) within a recess 906. In one example, the stem portion 916 can house the recess 906 for receiving the tunneling portion of the disclosure to transition the handle 902 and tunneling portion between a locked and an unlocked arrangement of the disclosure. The handle 902 of FIG. 17 can otherwise include features and components of any other handle of the disclosure and can be used in any of the devices and methods of the disclosure.

Figure 18A:
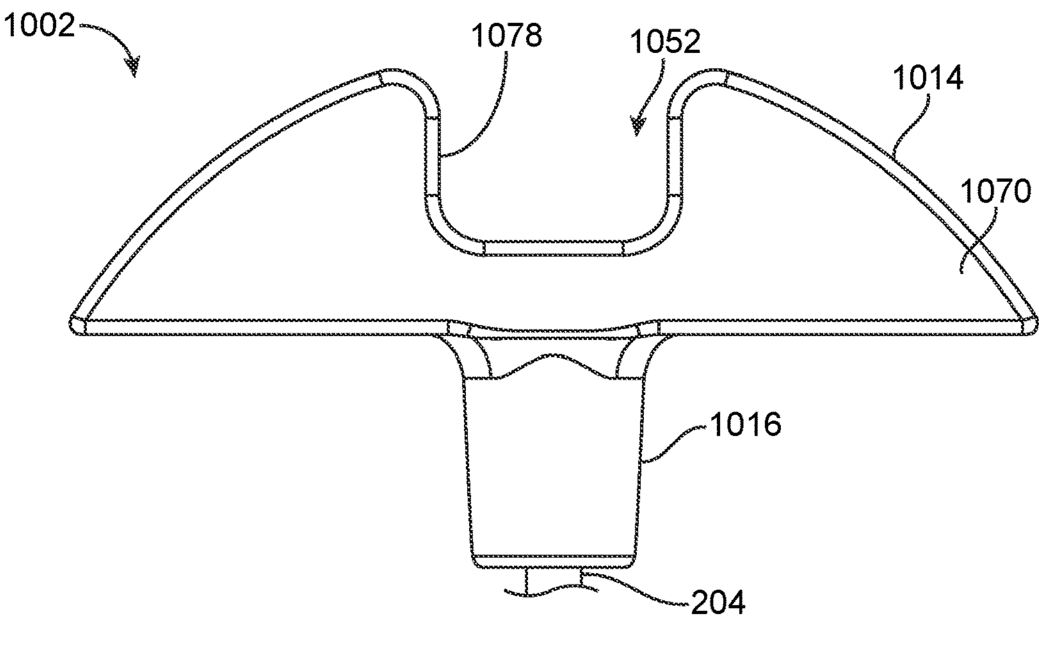
Figure 18B:
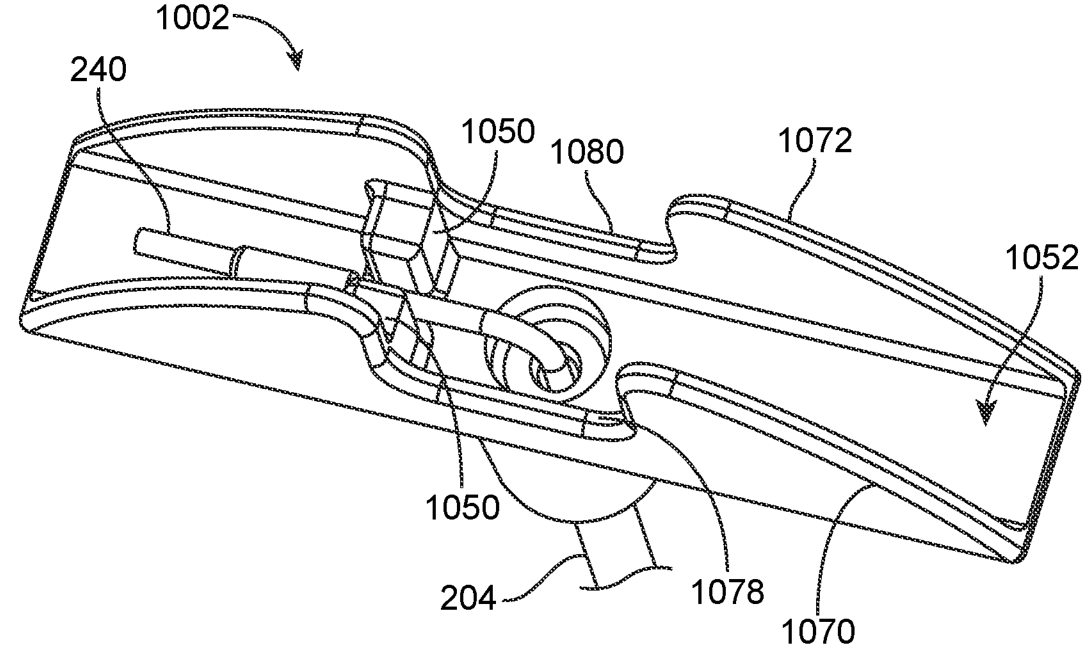

Referring now in addition to FIGS. 18A-18B, in another example, a handle 1002 can include a grip portion 1014 and a stem portion 1016. In some examples, the handle 1002 may comprise at least some of substantially the same features and attributes of the prior examples. In one example, the grip portion 1014 includes first and second opposing faces 1070, 1072, separated from a channel 1052 that may extend all or part of a length of the first and second faces 1070, 1072 (i.e. from one end of the grip portion 1014 to the other). In one example, the channel 1052 is similar to that of channel 252, 752 or 852. In various examples, the handle 1002 can be configured to retain a tunneling element 204 (see also, tunneling element 204 disclosed with respect to FIG. 2B) and transition the relationship between the tunneling element 204 and the handle 1002 between a locked and unlocked arrangement of the disclosure. Any other tunneling element of the disclosure can alternately be utilized. In some examples, similar to the embodiments of FIGS. 3 and 15-16), one or more retaining members 1050 can be provided within the channel 1052 to selectively retain the core 240 of the tunneling element 204 of the disclosure, if provided, via friction fit or the like in a locked position. In one example, the first and second faces 1070, 1072 can be parallel to each other. In one example, the faces 1070, 1072 are flared and/or increased in cross-section to improve comfort of grip. In various examples, one or more faces 1070, 1072 can include a notch 1078, 1080. In some examples, the notch(s) 1078, 1080 is aligned with the stem portion 1016. The handle 1002 of FIGS. 18A-18B can otherwise include features and components of any other handle of the disclosure and the handle and handle features of FIGS. 18A-18B be used in any of the devices and methods of the disclosure.

Referring now in addition to FIGS. 19A-19C, in another example, a tunneling device 1100 includes a handle 1102 and a tunneling element 1104 having a conduit 1122. In the illustrated example, the handle 1102 may comprise an asymmetrical shape/profile as viewed from one or more angles. In various examples, the tunneling element 1104 may engage the handle 1102 longitudinally at an off-center location (i.e. the tunneling element 1104 may be inserted within a recess of the handle 1120 located to the right or left of a central point C between ends 1103*a*, 1103*b* of a bottom 1120 the handle 102). In some examples, the tunneling device 1100 may comprise at least some of substantially the same features and attributes of the prior examples. In one example, the tunneling element 1104 is identical to tunneling element 104 disclosed in FIGS. 1A and 1C. In various examples, the handle 1102 can be configured to retain the tunneling element 1104 and transition the relationship between the tunneling element 1104 and the handle 1102 between a locked and unlocked arrangement of the disclosure. In one example, the conduit 1122 of the tunneling element 1104 has a square-shaped cross section and is sized to be received within a correspondingly-shaped (i.e. square) recess 1106 positioned within the bottom 1120 of the handle 1102. Any other tunneling element 1104 of the disclosure can alternately be utilized as long as the recess 1106 is complimentary shaped. In this example, the handle 1102 further includes a thumb rest 1115 at end 1103*a* on which a user's thumb T of a user's hand H may rest during operation of the tunneling device 1100. In one example, the thumb rest 1115 is opposing and parallel to the bottom 1120 of the handle 1102. In one example, in operation during a tunneling procedure such as any of those outlined herein, a user's hand is positioned such that their thumb T is on the thumb rest 1115 while their index finger is one side of the tunneling element 1104 and their remaining fingers on that hand (i.e. middle finger M, ring finger R and pinky finger P) are on the opposite side of the tunneling element 1104, against the bottom 1120, as is shown in FIG. 19A. In one example, the handle 1102 includes at least one face 1170 extending up from the bottom 1120. In one example, the face 1170 may be semicircular. In one example, the thumb rest 115 extends outwardly from the face 1170. In various examples, the other, opposing side of the handle 1102 is a mirror image of what is shown in FIG. 19A. The tunneling device 1100 of FIGS. 19A-19C can otherwise include features and components of any other handle of the disclosure and the tunneling device of FIGS. 19A-19C be used in any of the devices and methods of the disclosure.

Figure 20:
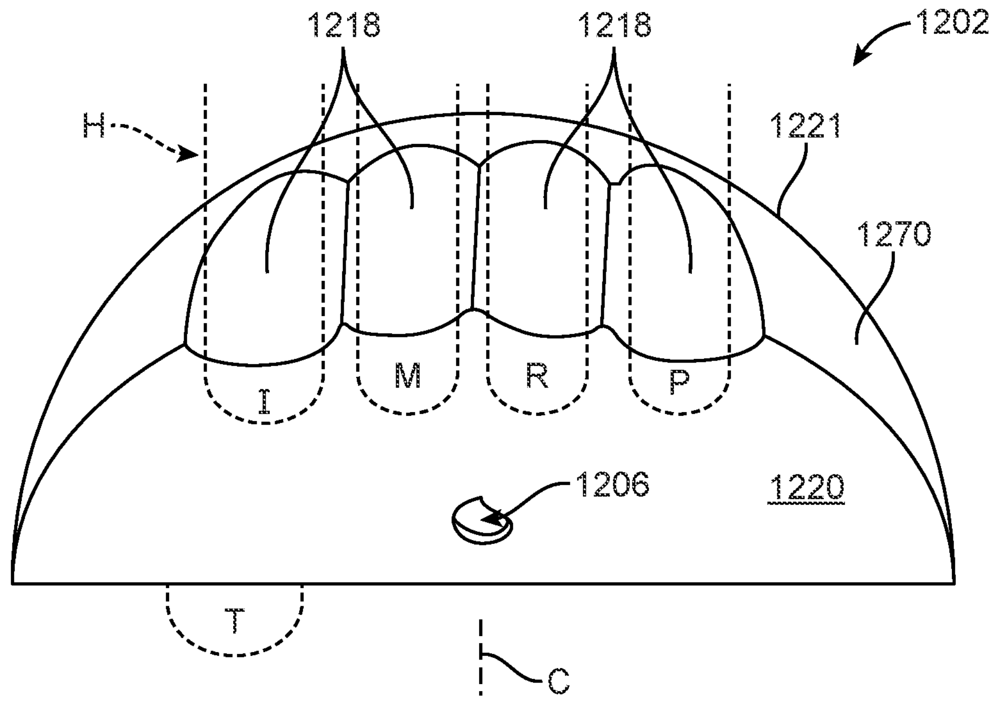
FIG. 20 is a bottom side view of an alternate example handle having a user's hand partially shown in dashed line.

Referring now in addition to FIG. 20, which illustrates an alternate handle 1202. In some examples, the handle 1202 of FIG. 20 may comprise at least some of substantially the same features and attributes of the prior examples. In various examples, the handle 1202 is asymmetrical as viewed from one or more angles. In some examples, the handle 1202 may comprise at least some of substantially the same features and attributes of the prior examples. In various examples, the handle 1202 can be configured to retain a tunneling element (see also, tunneling element 104 or 204 disclosed with respect to FIGS. 1A, 2B) within recess 1206 and transition the relationship between the tunneling element and the handle 1202 between a locked and unlocked arrangement of the disclosure. In this example, the handle 1202 further includes a plurality of indents 2118 (e.g., four indents) on which a user's finger (index finger I, middle finger M, ring finger R, pinky finger P) may rest during operation handle 1202. In one example, the indents are located on a side surface 1270 between a bottom 1220 and top surface (not visible but opposing bottom 1120 and at edge 1221, separated by side surface 1270). In one example, the top surface is identically configured as the bottom 1120 with the exception of the recess 1206. In one example, the recess 1206 is aligned with a longitudinal center C of the handle 1202. In one example, the bottom 1220 is generally crescent-shaped. In one example, a user's thumb T may be positioned at least partially on bottom 1220. In one example, in operation during a tunneling procedure such as any of those outlined herein, a user's hand H is positioned such that their at least one or more of their fingers (e.g., fingers T, I, M, R, P) are at least partially gripping the bottom 1220. The handle 1202 of FIG. 20 can otherwise include features and components of any other handle of the disclosure and used in any of the devices and methods of the disclosure.

Figure 21:
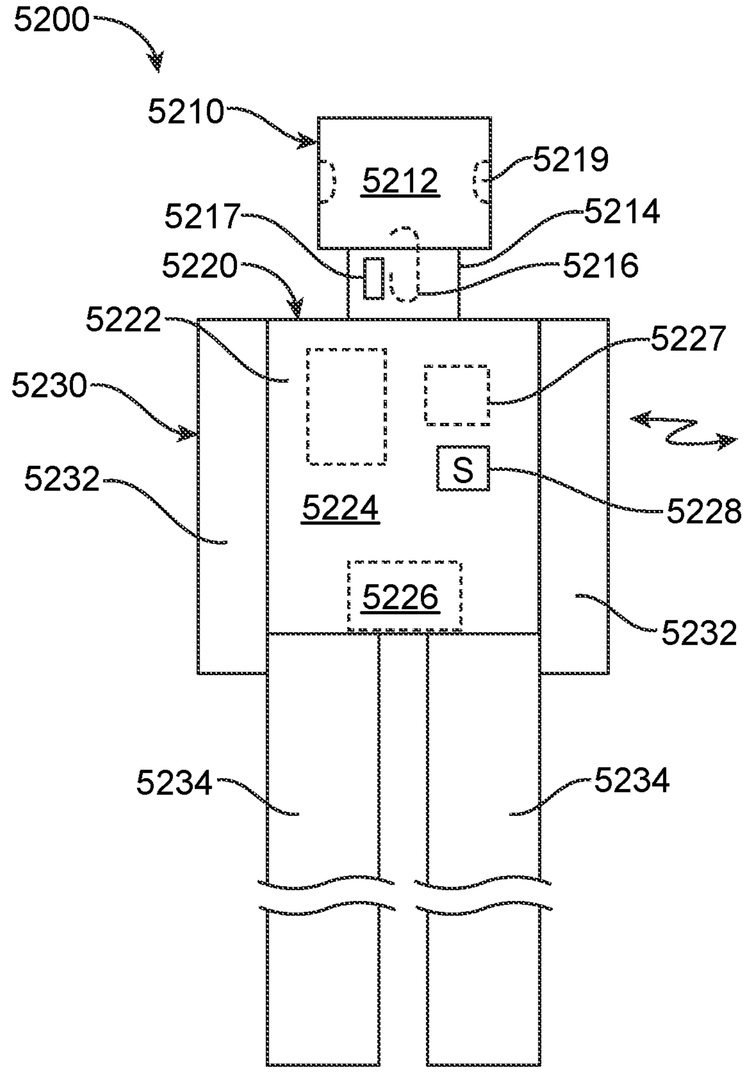
FIG. 21 is a diagram including a front view schematically representing a patient's body to which example methods and/or example devices may be applied.

Devices of the disclosure can be used to form a pathway in a patient's body for a variety of medical purposes, with the pathway (i.e. tunnel) located in a wide variety of locations. FIG. 21 schematically represents numerous example locations and body regions at which the pathway may be formed. As shown in FIG. 21, patient's body 5200 comprises a head-and-neck portion 5210, including head 5212 and neck 5214. Head 5212 comprises cranial tissue, nerves, brain, etc., which may include auditory portions 5219 (e.g., hearing organs, nerves) and upper airway 5216 (e.g., nerves, muscles, tissues), etc. As further shown in FIG. 21, the patient's body 5200 comprises a torso 5220, which comprises various organs, muscles, nerves, other tissues, such as but not limited to those in pectoral region 5222 (e.g., cardiac 5227), abdomen 5224, and/or pelvic region 5226 (e.g., urinary/bladder, anal, reproductive, etc.). As further shown in FIG. 21, the patient's body 5200 comprises limbs 5230, such as arms 5232 and legs 5234.

Figure 22:
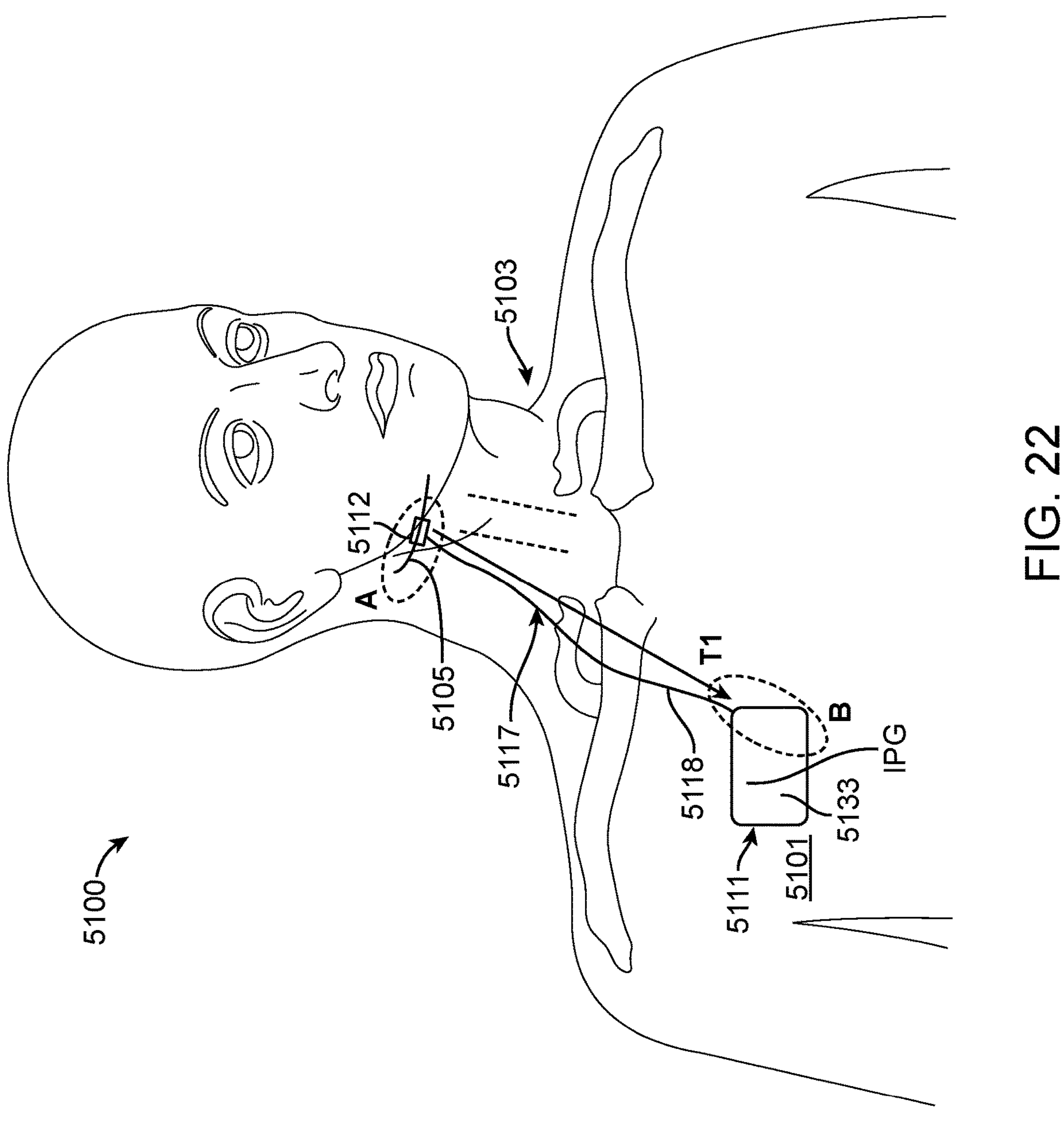
FIG. 22 is a diagram including a front view schematically representing a patient's body, tunneling path, and example implanted medical device.
Figure 23A:
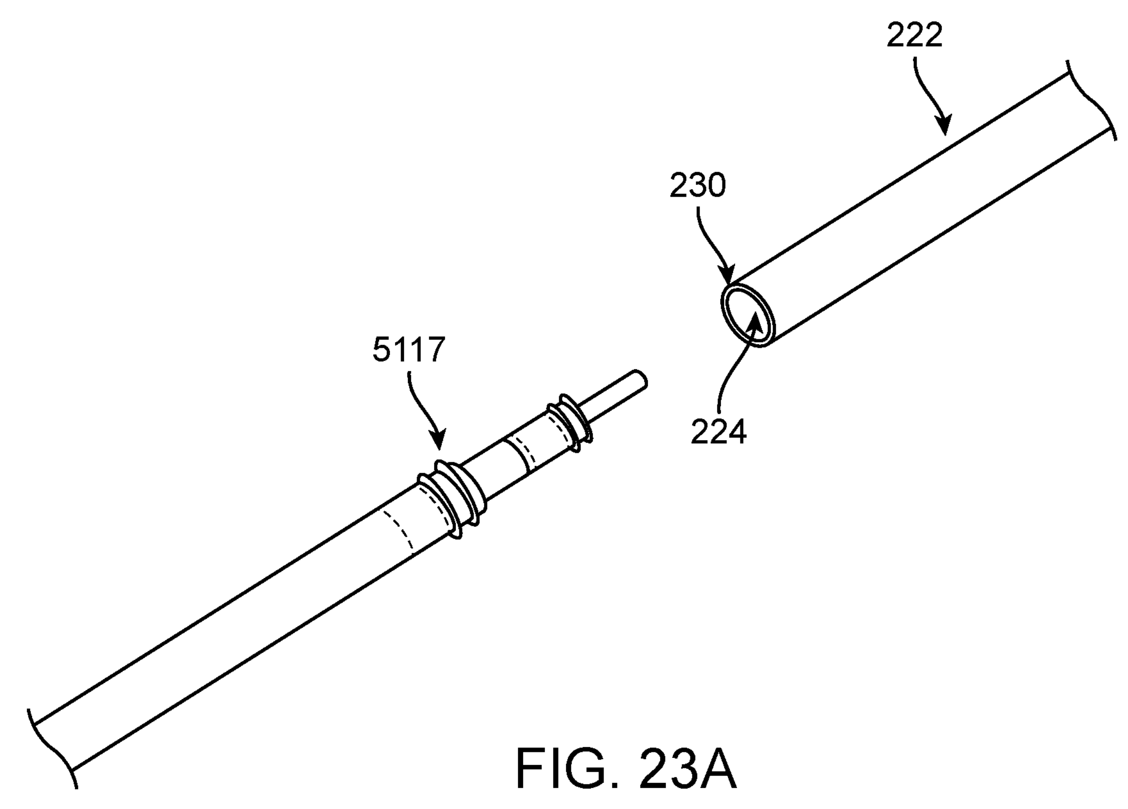
FIG. 23A is a partial, perspective view of a proximal end of a lead and a proximal end of a conduit, according to an example of the disclosure.
Figure 23B:
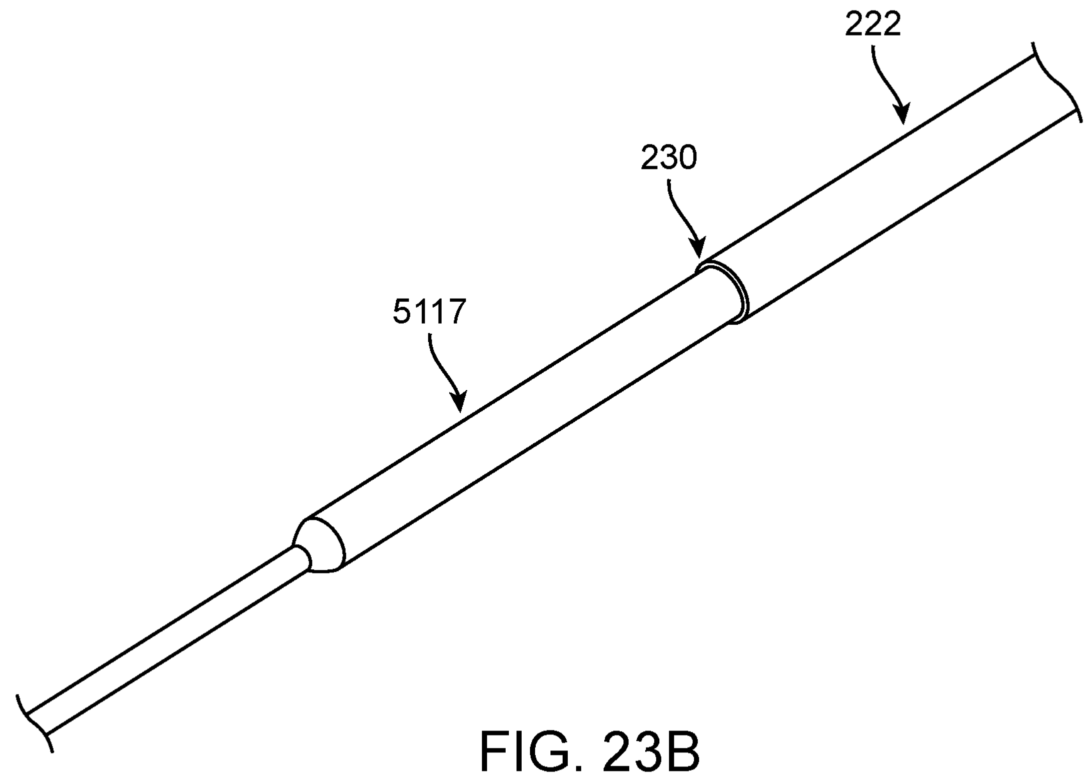
FIG. 23B is a partial, perspective view of the lead of FIG. 23A partially inserted into the conduit, according to an example of the disclosure.

FIG. 22 is a diagram schematically representing an example stimulation device 5113 (e.g. neurostimulation) and lead 5117 implanted within a patient body. As shown in FIG. 22, the stimulation device 5113 may comprise an implantable pulse generator (IPG) 5133 and the lead 5117 may comprise a lead body 5118 and an element 5112. In some examples, the element 5112 may comprise a stimulation electrode arrangement. In the particular example, the element 5112 is subcutaneously implanted and engaged relative to an upper airway patency-related nerve 5105 such as, but not limited to, the hypoglossal nerve. In some examples, the IPG 5133 is implanted in the pectoral region 5101 with stimulation lead 5117 extending upward into the head-and-neck region 5103. In some examples in which the element 5112 comprises a stimulation electrode arrangement it is chronically implantable, and may comprise a cylindrical arrangement to be at least partially wrapped about a nerve, may comprise a paddle-style electrode, may comprise a non-cuff configuration, or other configuration by which electrode may be chronically implanted in nerve-stimulating relation to the nerve.

It will be understood that the lead 5117 may be used for sensing, with or without stimulation, and may communicate power, sensed information, stimulation control signals, other control signals, and/or other signals between the element 5112 and the pulse generator (or other element for control, power, and/or communication, etc.).

As further shown in FIG. 22, in some examples an implantation procedure may comprise surgically creating an implant-access incision A near the target nerve (or other tissue) at which the element 5112) is to be located and a second implant-access incision B near a location at which the IPG 5133 will be implanted, such as within a pocket formed within the pectoral region. Among other steps, after forming the respective implant-access incisions A, B, one of the example tunneling devices of the present disclosure may be used to form a tunnel/pathway (as represented by arrow T1) subcutaneously along a path between the implant-access incisions A, B. While some more specific example tunneling examples are described below in association with at least FIGS. 24A-29, one example implantation method (associated with example tunneling methods) will be described.

In particular, in some examples, upon formation of tunnel T1, the tunneling device remains positioned within the tunnel T1 with tip (e.g. 108 in FIG. 1A) exposed at/outside of implant-access incision B and with at least a handle (e.g. 102 in FIG. 1A) exposed at/outside of implant-access incision A. The handle is removed from a proximal end (e.g. 112 in FIG. 1A) of a tunneling element (e.g. 104) and a proximal end of lead 5117 is removably connected (e.g. inserted or otherwise engaged) relative to a proximal end of the tunneling element. As further shown in FIGS. 23A-23B, in one example, a proximal end of lead 5117 becomes removably connected (e.g. removably inserted relative to the distal end 230 of tunneling element 204 and maintained therein via friction) to provide temporary connection to pull lead 5117 within and through tunnel T1 to a desired location. In another example, the tunneling element (e.g., tunneling element 204) can be configured to grasp the lead 5117 or could be configured to have a side recess in the conduit that could help retain the lead 5117. Thereafter, the distal end 110 of the tunneling element is pulled through implant-access incision B and further out of the patient's body, which in turn acts to pull the proximal end (e.g. 112) of the tunneling element further into the tunnel T1 and necessarily also pulls the proximal end of the lead 5117 into and through the tunnel T1. This motion is continued until the tunneling element is completely removed from the tunnel T1 and the proximal end of the lead 5117 is at the implant-access incision B, where it can be separated from the proximal end of the tunneling element. Thereafter, the proximal end of the lead 5117 may be connected to the IPG 5133 before the IPG 5133 is positioned for chronic implantation within the pre-formed pocket within the pectoral region or other bodily region (e.g., back, buttocks, underarm area, etc.). Furthermore, with the proximal end of the lead 5117 in this position and the body 5118 of the lead 5117 extending within and through tunnel T1, a distal end of the lead 5117 (including element 5112) will be located adjacent to implant-access incision A, whereupon the element 5112 (and/or sensor) may be maneuvered into a desired position relative to the target nerve 5105 and/or other target tissue or other implantable devices (power, control signal transmission).

Referring now in addition to FIGS. 24A-29, which collectively outline additional example methods of the disclosure. In some examples, such example methods may be implemented via at least some of substantially the same features and attributes of the example devices of FIGS. 1A-23B. Various example methods 6000 include a step of directing a distal end of a tunneling device through an incision of a body of a patient 6002 to form a tunnel or pathway toward an implant location (at 6004) for an implanted medical device 6004. In one example, the method includes bending the conduit prior to the step of directing the distal end of the tunneling device 6135 (FIG. 29). In some examples, the conduit pre-bent or is in a curved arrangement (e.g., the arrangement of FIG. 2C or similar) prior to the step of directing the distal end of the tunneling device. In an example, the tunneling element (e.g., conduit of the tunneling element) may be arranged in a curved configuration prior to the step of directing or inserting the distal end through the incision and into the body. In one non-limiting example, the incision is located within a neck of the body such as, but not limited to, implant incision A in FIG. 22. The tunneling device can be any of the disclosure. In one example, the tunneling device includes a conduit and a handle that can be selectively connected to the conduit in a locked arrangement in which a rotational position of the handle is locked with respect to the conduit/tunneling element (and vice versa). In some examples, the method may further include advancing the distal end of the tunneling device into the body 6004, rotating or maneuvering the handle with respect to the conduit/tunneling element to a different rotational position 6008. In one example, the step of maneuvering includes rotating the handle to the different rotational position with respect to the tunneling element without separating the handle from the tunneling element. Method 6000 can include, in some examples, further advancing the distal end of the tunneling device into the body 6012. In some examples, the distal end is directed/advanced to an implanted pulse generator within the body of the patient, which may be connected to a nerve. In non-limiting examples, the pulse generator may be implanted at any location.

Figures 24A, 24B, 24C, 25:
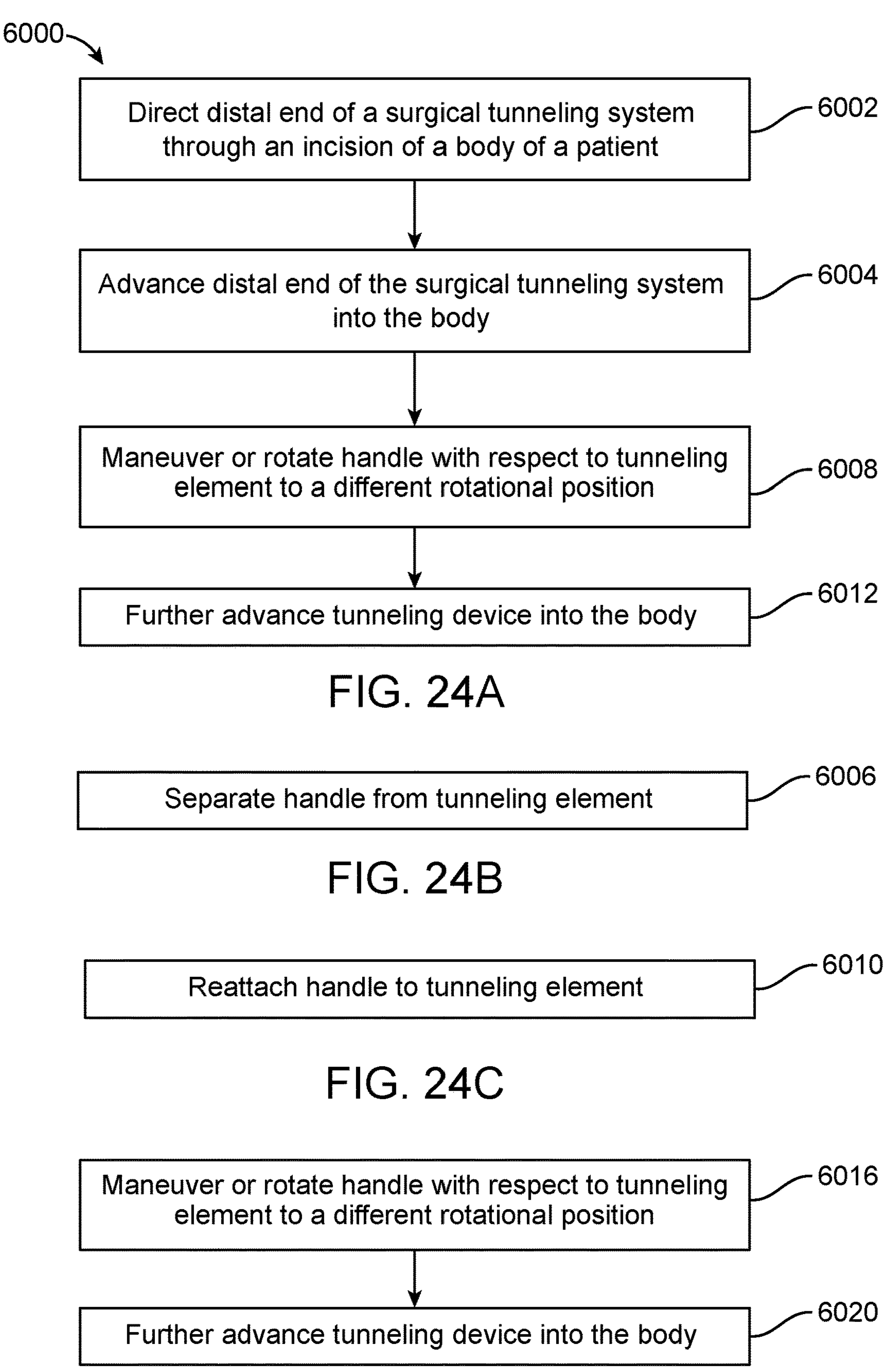

Referring in addition to FIG. 24B, some examples will include separating the handle from the conduit to transition the tunneling device into an unlocked arrangement 6006 prior to maneuvering the handle with respect to the tunneling element 6008. Such examples can further include a step of reattaching the handle to the tunneling element 6010 after maneuvering the handle with respect to the tunneling element to a different rotational position 6008 (FIG. 24C).

During an example procedure of the disclosure, the handle may be gripped by a clinician to manipulate the tunneling element and apply torque to the tunneling element to form the pathway. Advancing the distal end of the tunneling device subcutaneously through the patient's body may comprise rotating or maneuvering the handle to facilitate directional maneuvering/advancement of the conduit within the patient's body (e.g., among, through, subcutaneous tissues, structures) as forming the pathway. One significant benefit of aspects of the disclosure is that a clinician can adjust the rotational orientation of the handle with respect to the tunneling element as desired throughout a procedure as many or as few times as they desire to achieve the most effective tunneling and ergonomic effect during a tunneling procedure from an incision to a target site (e.g., to an implanted pulse generator or other implanted medical device implant site). Therefore, the degree of adjustment and number of adjustments is customizable. In some examples, handle is rotated a degree less than 360 degrees, less than 180 degrees, or less than 90 degrees for each rotational adjustment. Further, as outlined at least in FIG. 25, additional steps of removing the handle 6014, rotating or maneuvering the handle with respect to the tunneling element to a different rotational position 6016, and further advancing the distal end of the tunneling device into the body 6020 can be repeated as many times throughout a tunneling procedure (e.g., method 6000). In one example, the conduit does not rotate relative to the patient or rotates minimally (i.e. +/−5 degrees) while the handle is re-positioned. As applicable, the steps of FIGS. 24B and 24C can additionally be repeated and incorporated into the method of FIG. 25 in various examples of the disclosure as a clinician continues to adjust the rotational angle of the handle with respect to the tunneling element to achieve the clinician's preferred ergonomic characteristics.

In some examples, the tunneling element (e.g., tunneling element 104) has an electrocautery distal tip (e.g., tip 108). The electrocautery distal tip can, in some examples, be selectively activated to cauterize tissue during a tunneling procedure. In some examples including a core, the core (e.g., core 240) can include an electrocautery distal tip 242. The electrocautery distal tip 242 can, in some examples, be selectively activated to cauterize tissue during a tunneling procedure. In examples utilizing an electrocautery tip of sorts, the tunneling device would be configured to include or connect to a power source to selectively direct power to energize the electrocautery distal tip. In various examples, methods of the disclosure may include utilizing the electrocautery distal tip. As the pathway is formed and tunneling is conducted, it is possible that tissue along the pathway may bleed. In this instance, some example methods include cauterizing tissue in attempts to stop such bleeding 6130 (FIG. 26).

Once the tunneling device is at a target site/implant location (e.g., at or adjacent an implanted medical device), some example methods will include pulling a lead through the formed pathway with the conduit of the tunneling element 6134 (FIG. 28, see also, FIGS. 23A-23B) and removing the lead from the conduit and connecting the lead to the implantable pulse generator. In some examples, the lead is pulled in a proximal direction relative to the conduit and handle. As shown in the transition from FIG. 23A to FIG. 23B, with further reference to FIG. 27, in one example, the lead 5117 is inserted at least partially within the channel 224 of the conduit 222 prior to the step of pulling 6132. In some examples, a core (e.g., core 240 may be withdrawn to provide space for the lead 5117. In other examples, a distal tip (e.g., distal tip 108) may be removed from the tunneling element (e.g., tunneling element 104) so that the lead 5117 can be inserted within space provided by the tunneling element. The lead 5117 may, in some examples, be maintained within the channel 224 via a friction fit or the like.

EXAMPLES

An example method comprises directing a distal end of a surgical device through an incision of a body of a patient, the surgical device including a tunneling element and a handle selectively connected to the tunneling element; advancing the distal end of the tunneling element into the body; maneuvering the handle to a different rotational position with respect to the tunneling element; and further advancing the tunneling element into the body.

The example method can further include advancing the distal end of the tunneling element into the body by directing the distal end of the tunneling element to an implant location of an implantable pulse generator within the body of the patient.

In some examples, the incision is in a neck of the body of the patient.

The example method can further include cauterizing tissue of the patient with a distal tip of the tunneling element.

In some examples, the tunneling element is tubular.

The example method can further include advancing the distal end of the tunneling element by rotating the tunneling element within the body via rotating the handle.

The example method can further include advancing the distal end of the tunneling element into the body to form a tunnel in the body, the tunneling element comprising a conduit, removing the handle from a proximal end of the conduit, removably inserting a proximal end of a lead relative to a proximal end of the conduit, and pulling the lead through the tunnel with the conduit.

The example method can further include removing the conduit from the lead and from the body while leaving the lead within the tunnel within the body and connecting the proximal end of the lead to an implantable pulse generator.

The example method can further include bending the conduit prior to the step of directing.

In some examples, the conduit is in a curved arrangement prior to the step of directing.

The example method can further include maneuvering the handle by separating the handle from the tunneling element, rotating the handle to the different rotational position with respect to the tunneling element, and reattaching the handle to the tunneling element.

The example method can further include maneuvering the handle by rotating the handle to the different rotational position with respect to the tunneling element without separating the handle from the tunneling element.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

What is claimed is:

1. A surgical device comprising:

a tunneling element comprising a conduit, the conduit comprising a proximal end portion comprising a first polygonal cross-sectional shape which extends through an utmost proximal end of the tunneling element;

a handle comprising a recess, the recess including a second polygonal cross-sectional shape corresponding to the first polygonal cross-sectional shape and configured to:

releasably engage the first polygonal cross-sectional shape of the tunneling element to cause the handle to be selectively locked into one of a plurality of different rotationally lockable positions relative to an outer surface of the tunneling element to cause a locked arrangement by which torquing of the handle is to be transmitted to the tunneling element; and selectively disengage from the outer surface of the tunneling element into an unlocked arrangement by which the handle is selectively adjustable into a respective one of the plurality of different rotationally lockable positions with respect to the outer surface of the tunneling element.

2. The surgical device of claim 1, wherein the conduit comprises a channel and wherein the tunneling element comprises a core slidably removable within the channel throughout a length of the conduit.

3. The surgical device of claim 2, wherein the core is configured to be longitudinally moveable with respect to the handle when the surgical device is in the locked arrangement.

4. The surgical device of claim 2, wherein a longitudinal position of the core is configured to be locked with respect to the conduit.

5. The surgical device of claim 2, wherein, in the locked arrangement, the core is rotationally locked with respect to the handle.

6. The surgical device of claim 1, wherein the handle includes a grip portion and a stem extending from the grip portion, the stem including the recess.

7. The surgical device of claim 6, wherein, when the tunneling element is fixed to the handle, the tunneling element forms athe locking engagement with the handle at a location distal to the grip portion.

8. The surgical device of claim 1, the handle further including a lock configured to engage the tunneling element in the locked arrangement.

9. The surgical device of claim 1, wherein the handle includes a side aperture in which a lock is received, the lock being a screw that engages the tunneling element.

10. The surgical device of claim 1, wherein the plurality of different rotationally lockable positions are in increments ranging from 10 to 120 degrees.

11. The surgical device of claim 1, wherein a number of the plurality of different rotationally lockable positions is equal to or less than 8.

12. A surgical device comprising:

a tunneling element defining a conduit which comprises an outer surface, wherein the outer surface includes a plurality of first mating elements proximate a proximal end portion of the tunneling element, wherein the plurality of first mating elements are circumferentially spaced apart on the outer surface; and a handle comprising a second mating element configured to:

releasably engage a respective one of the plurality of first mating elements to selectively lock the handle into one of a plurality of different rotationally lockable positions relative to the outer surface of the tunneling element to cause a locked arrangement by which torquing of the handle is to be transmitted to the tunneling element; and selectively disengage from the respective one of the plurality of first mating elements into an unlocked arrangement by which the handle is selectively adjustable into a respective one of the plurality of different rotationally lockable positions with respect to the outer surface of the tunneling element.

13. The surgical device of claim 12 wherein the handle comprises a recess, which comprises the second mating element.

14. The surgical device of claim 13, wherein each respective one of the plurality of first mating elements of the tunneling element comprises a protrusion, and wherein the plurality of first mating elements comprise a number selected to designate a finite number of the plurality of different rotationally lockable positions.

15. The surgical device of claim 13, wherein each respective one of the plurality of first mating elements of the tunneling element comprises at least one of an indent, an aperture, or a pocket, and wherein the plurality of first mating elements comprise a number selected to designate a finite number of the plurality of different rotationally lockable positions.

16. The surgical device of claim 13, wherein the handle includes a grip portion and a stem extending from the grip portion, wherein the stem comprises the recess.

17. A surgical device comprising:

a tunneling element defining a conduit comprising an outer surface, the outer surface including a key at an utmost proximal end of the tunneling element; and a handle comprising a recess, wherein the key of the tunneling element and the recess of the handle are configured to:

releasably engage each other to selectively lock the handle into one of a plurality of different rotationally lockable positions relative to the outer surface of the tunneling element to cause a locked arrangement which prevents rotation of the tunneling element with respect to the handle and by which torquing of the handle is to be transmitted to the tunneling element; and selectively disengage from each other into an unlocked arrangement by which the handle is selectively adjustable into a respective one of the plurality of different rotationally lockable positions with respect to the outer surface of the tunneling element.

18. The surgical device of claim 17, wherein the key comprises a cross-sectional circular shape and a protrusion.

19. The surgical device of claim 18, wherein the recess includes a plurality of pockets each sized to selectively receive the protrusion of the key, wherein each respective one of the plurality of pockets corresponds to a respective one of the plurality of different rotationally lockable positions of the handle relative to the tunneling element.

20. The surgical device of claim 17, wherein the handle includes a grip portion and a stem extending from the grip portion, wherein the stem includes the recess.

21. The surgical device of claim 17, wherein the plurality of different rotationally lockable positions includes at least two different rotationally lockable positions at least 90 degrees apart.

* * * * *